United States Patent
Zapol et al.

(10) Patent No.: US 8,887,721 B2
(45) Date of Patent: Nov. 18, 2014

(54) ATTENUATION OF VASOACTIVE OXYGEN CARRIER-INDUCED VASOCONSTRICTION

(75) Inventors: Warren M. Zapol, Cambridge, MA (US); Binglan Yu, Arlington, MA (US); Fumito Ichinose, Brookline, MA (US)

(73) Assignee: The General Hospital Corporation, Boston, MA (US)

(*) Notice: Subject to any disclaimer, the term of this patent is extended or adjusted under 35 U.S.C. 154(b) by 941 days.

(21) Appl. No.: 12/513,624

(22) PCT Filed: Nov. 6, 2007

(86) PCT No.: PCT/US2007/083746
§ 371 (c)(1),
(2), (4) Date: Oct. 8, 2009

(87) PCT Pub. No.: WO2008/063868
PCT Pub. Date: May 29, 2008

(65) Prior Publication Data
US 2010/0051025 A1 Mar. 4, 2010

Related U.S. Application Data

(60) Provisional application No. 60/864,734, filed on Nov. 7, 2006.

(51) Int. Cl.
*A61M 16/10* (2006.01)
*A61M 16/20* (2006.01)
(Continued)

(52) U.S. Cl.
CPC ............... *A61K 33/00* (2013.01); *A61M 16/12* (2013.01); *A61K 45/06* (2013.01); *A61M* (Continued)

(58) Field of Classification Search
CPC . A61K 2300/00; A61K 31/555; A61K 38/42; A61K 33/30; A61K 33/26; A61K 33/00; A61K 31/195; A61K 31/355; A61K 31/505; A61K 31/525; A61K 31/60; A61K 33/04; A61K 33/06; A61K 31/28; A61K 31/30; A61K 31/315; A61K 38/00; A61K 9/209; A61K 45/06; A61K 9/0026; A61K 9/1271; A61J 3/07; A61M 16/12; A61M 16/208; A61M 2016/003; A61M 2016/0039; A61M 2016/1035; A61M 2202/0275
USPC ............ 128/200.24, 203.12, 203.15, 203.25, 128/204.18, 204.21, 204.23, 205.11; 424/718; 514/13.4; 530/385
See application file for complete search history.

(56) References Cited

U.S. PATENT DOCUMENTS 5,396,882 A 3/1995 Zapol
5,485,827 A * 1/1996 Zapol et al. .............. 128/200.14
(Continued)

FOREIGN PATENT DOCUMENTS

CN 1229677 A 9/1999
WO WO 93/16721 9/1993
(Continued)

OTHER PUBLICATIONS

Muir et al., "Hemoglobin Solutions and Tissue Oxygenation," J. Vet. Intern. Med. 7:127-135 (2003); Abstract, p. 128, RBC substitute solutons; p. 129, role of NO; p. 130, Table 1; p. 131, therapeutic applications of HBOC's.

(Continued)

*Primary Examiner* — Annette Dixon
(74) *Attorney, Agent, or Firm* — Fish & Richardson P.C.

(57) ABSTRACT

Compositions and methods for preventing or reducing vasoconstriction in a mammal following administration of an artificial oxygen carrier (e.g., a hemoglobin-based oxygen carrier) are disclosed. The methods include administering to a mammal a composition containing an artificial oxygen carrier in combination with one or more of a nitric oxide-releasing compound, a therapeutic gas containing gaseous nitric oxide, a phosphodiesterase inhibitor, and/or a soluble guanylate cyclase sensitizer.

81 Claims, 22 Drawing Sheets

(51) Int. Cl.
*A61M 16/12* (2006.01)
*A61K 45/06* (2006.01)
*A61K 38/42* (2006.01)
*A61K 33/00* (2006.01)
*A61M 16/00* (2006.01)

(52) U.S. Cl.
CPC ......... *2202/0275* (2013.01); *A61M 2016/1035* (2013.01); *A61M 2016/003* (2013.01); *A61K 38/42* (2013.01); *A61M 16/208* (2013.01); *A61M 2016/0039* (2013.01)
USPC ............. 128/203.15; 128/203.12; 128/200.24

(56) References Cited

U.S. PATENT DOCUMENTS

| | | | |
|---|---|---|---|
| 5,531,218 A | 7/1996 | Krebs | |
| 5,536,241 A | 7/1996 | Zapol | |
| 5,540,233 A * | 7/1996 | Larsson et al. | 600/538 |
| 5,558,083 A * | 9/1996 | Bathe et al. | 128/203.12 |
| 5,570,683 A * | 11/1996 | Zapol | 128/200.14 |
| 5,823,180 A * | 10/1998 | Zapol | 128/200.24 |
| 5,839,433 A | 11/1998 | Higenbottam | |
| 5,873,359 A * | 2/1999 | Zapol et al. | 128/203.12 |
| 5,885,621 A | 3/1999 | Head et al. | |
| 5,900,402 A | 5/1999 | Shorr | |
| 5,904,938 A | 5/1999 | Zapol et al. | |
| 6,063,027 A * | 5/2000 | Alving et al. | 600/300 |
| 6,063,407 A | 5/2000 | Zapol et al. | |
| 6,089,229 A * | 7/2000 | Bathe et al. | 128/204.21 |
| 6,103,690 A | 8/2000 | Kilbourn et al. | |
| 6,139,506 A * | 10/2000 | Heinonen | 600/532 |
| 6,323,175 B1 * | 11/2001 | Hsia | 424/450 |
| 6,601,580 B1 | 8/2003 | Bloch et al. | |
| 6,656,452 B1 | 12/2003 | Zapol et al. | |
| 6,811,768 B2 | 11/2004 | Zapol et al. | |
| 6,894,150 B1 * | 5/2005 | Tye | 530/402 |
| 6,935,334 B2 | 8/2005 | Bloch et al. | |
| 7,267,817 B2 * | 9/2007 | Page et al. | 424/93.73 |
| 7,516,742 B2 * | 4/2009 | Stenzler et al. | 128/204.23 |
| 7,530,353 B2 * | 5/2009 | Choncholas et al. | 128/204.18 |
| 2005/0234030 A1 * | 10/2005 | Bartolini et al. | 514/183 |
| 2005/0255178 A1 | 11/2005 | Bloch et al. | |
| 2006/0182815 A1 * | 8/2006 | Gladwin et al. | 424/718 |
| 2006/0207594 A1 | 9/2006 | Stenzler et al. | |
| 2007/0154569 A1 * | 7/2007 | Gladwin et al. | 424/718 |

FOREIGN PATENT DOCUMENTS

| | | |
|---|---|---|
| WO | 9808500 | 3/1998 |
| WO | WO 2006/037491 | 4/2006 |

OTHER PUBLICATIONS

Roberts et al., "Inhaled nitric oxide reverses pulmonary vasoconstriction in the hypoxic and acidotic newborn lamb." Circulation Research 72:246-254 (1993); Abstract, p. 247, materials and methods; p. 248, NO-treatment protocols; p. 251, Discussion.

Sampei et al., "Role of nitric oxide scavenging in vascular response to cell-free hemoglobin transfusion," Am J Physiol Heart Circ Physiol. 289:H1191-H1201 (May 13, 2005); XP002572119.

Tsai et al., "Dissociation of local nitric oxide concentration and vasoconstriction in the presence of cell-free hemoglobin oxygen carriers," Blood 108(10):3603-3610 (Jul. 20, 2006); XP002572120.

Gladwin, M.T. et al., "The biochemistry of nitric oxide, nitrite, and hemoglobin: role in blood flow regulation," *Free Radical Biology & Medicine*, (2004) 36(6):707-717.

Hataishi R., et al., "Inhaled nitric oxide decreases infarction size and improves left ventricular function in a murine model of myocardial ischemia-reperfusion injury," *Am. J Physiol. Heart Circ. Physiol.*; (2006) 291(1):H379-84.

Imai, S., "Mechanisms of vasolidation of so-called nitrite compounds," *J. Clin. and Experimental Medicine*, (1989) 148(2):71-74 (with excerpted English translation).

Minneci P.C. et al "Hemolysis-associated endothelial dysfunction mediated by accelerated NO inactivation by decompartmentalized oxyhemoglobin," *J Clin. Invest.*; (2005) 115(12):3409-3417.

Sefton, W. et al., "Inhaled nitric oxide attenuates increased pulmonary artery pressure following diaspirin crosslinked hemoglobin (DCLHB) administration," *Artificial Cells, Blood Substitutes, and Immobilization Biotechnology*, (1999) 27(3):203-213.

Sowemino-Coker, S.O., "Red blood cell hemolysis during processing," *Transfus Med. Rev.*; (2002) 16(1):46-60.

Office Action issued in JP2009-536435 on Sep. 17, 2014 (4 pages).

Shimouchi and Kunieda, "Nitric oxide inhalation: a new selective pulmonary vasodilation method," Respiration Research, 14(7):690-696 (1995) (with English translation of abstract).

\* cited by examiner

ATTENUATION OF VASOACTIVE OXYGEN CARRIER-INDUCED VASOCONSTRICTION

CROSS-REFERENCE TO RELATED APPLICATIONS

This application is a national phase filing under 35 U.S.C. §371 of international application number PCT/US2007/083746, filed Nov. 6, 2007, which claims priority from U.S. Provisional Application No. 60/864,734, filed Nov. 7, 2006. The entire content of the prior applications are incorporated herein by reference.

STATEMENT AS TO FEDERALLY SPONSORED RESEARCH

This invention was made with Government support under grant number 5R01HL042397-17 awarded by the National Institutes of Health/National Heart, Lung, and Blood Institute. The Government may have certain rights in the invention.

FIELD OF THE INVENTION

This invention relates to compositions and methods for preventing or reducing vasoconstriction in a mammal following administration of a vasoactive oxygen carrier.

BACKGROUND

Red blood cells reversibly bind oxygen under physiological conditions and mediate the continuous delivery of oxygen to the tissues that is needed for cellular respiration. Blood transfusion constitutes a traditional treatment option for patients exhibiting red blood cell deficiency. Blood substitutes (i.e., artificial oxygen carriers) have been proposed as a cell-free means of avoiding the transmission of infectious agents (e.g., human immunodeficiency virus or hepatitis virus) that can accompany blood transfusion. In addition, blood substitutes can also be advantageous over allogeneic red blood cell transfusion in that the lack of iso-agglutinating antigens in blood substitutes obviates the need for blood typing and screening and avoids potentially adverse reactions that can result from a mismatch of the donor blood and the transfusion recipient. The lack of cross-matching requirements allows virtually immediate availability for transfusion of a blood substitute in the critical early periods of trauma or hemorrhage. Blood substitutes can also undergo storage for prolonged periods and retain their activity. See, e.g., Spahn et al. (2005) *Curr Pharm Des.* 11(31):4099 and Greenburg et al. (2004) *Crit. Care* 8 Suppl 2:S61.

A heme-based oxygen carrier is a cell-free blood substitute that contains heme combined with a native or modified protein (e.g., globin or albumin) or other molecule and that is capable of delivering oxygen to tissues. Heme-based oxygen carriers (e.g., hemoglobin-based oxygen carriers) can be used, for example, to prevent or treat hypoxia resulting from anemia, blood loss (e.g., from acute hemorrhage or during surgical operations), or shock (e.g., volume deficiency shock, anaphylactic shock, septic shock, or allergic shock). Heme-based oxygen carriers can be infused for essentially any purpose for which banked blood is administered to patients. See, e.g., Artificial Oxygen Carrier: Its Front Line (Koichi Kobayashi et al. eds., 2005). In addition, heme-based oxygen carriers can be administered to a subject to improve myocardial function and reduce myocardial infarct size after acute coronary ischemia and reperfusion. George et al. (2006) *Am. J. Physiol. Heart Circ. Physiol.* 291(3):H1126-37 and Caswell et al. (2005) *Am. J. Physiol. Heart Circ. Physiol.* 288:H1796-1801. Despite the foregoing advantages, administration of heme-based oxygen carriers often triggers vasoconstriction in recipients. This may account for the excess mortality due to heart attacks and strokes in clinical trials using hemoglobin-based oxygen carriers. Vasoconstriction due to heme-based oxygen carriers can cause coronary vasospasm, cerebral vasospasm, pulmonary vasospasm, renal vasospasm, and spasm of any or all other blood vessels and smooth muscles in the body, including those of the gastrointestinal tract.

SUMMARY

The invention is based, at least in part, on the surprising discovery that inhalation of nitric oxide prior to administering a heme-based oxygen carrier to a mammal can prevent or reduce the occurrence of vasoconstriction in the mammal without causing significant conversion of the administered ferrous heme-containing (active) compound to a ferric heme-containing (inactive) compound. The invention is also based, at least in part, on the surprising discovery that continued inhalation of nitric oxide at a low concentration subsequent to administration of a heme-based oxygen carrier can prevent or reduce the occurrence of pulmonary and systemic vasoconstriction in the mammal, also without causing significant conversion of the administered active ferrous heme to inactive ferric heme.

Disclosed are methods of preventing or reducing vasoconstriction in a mammal following administration (single or repeated) of a vasoactive oxygen carrier (e.g., a heme-based oxygen carrier such as a hemoglobin-based oxygen carrier) by: (i) administering to a mammal a nitric oxide-releasing compound (e.g., a nitrite) or a therapeutic gas containing gaseous nitric oxide; and (ii) administering to the mammal, during or after administration of the nitric oxide-releasing compound or the therapeutic gas, a composition containing a vasoactive oxygen carrier, wherein the nitric oxide-releasing compound or the gaseous nitric oxide is administered in an amount effective to prevent or reduce the occurrence of vasoconstriction in the mammal following administration of the composition containing the vasoactive oxygen carrier.

Also disclosed is the use of gaseous nitric oxide for the preparation of a therapeutic gas for preventing or reducing the occurrence of vasoconstriction in a mammal following administration of a composition containing a vasoactive oxygen carrier (e.g., a heme-based oxygen carrier such as a hemoglobin-based oxygen carrier).

Also disclosed is the use of a nitric oxide-releasing compound (e.g., a nitrite) for the preparation of a therapeutic composition for preventing or reducing the occurrence of vasoconstriction in a mammal following administration of a composition containing a vasoactive oxygen carrier (e.g., a heme-based oxygen carrier such as a hemoglobin-based oxygen carrier).

The therapeutic gas can be administered to the mammal by, for example, inhalation, an artificial lung, or an aqueous solution containing dissolved nitric oxide.

The concentration of gaseous nitric oxide in the therapeutic gas can be, for example, at least 20 ppm, at least 40 ppm, at least 50 ppm, at least 80 ppm, at least 100 ppm, at least 200 ppm, at least 300 ppm, or at least 500 ppm. In some embodiments, the concentration of gaseous nitric oxide in the therapeutic gas is in the range of 50 ppm to 500 ppm (e.g., 60 ppm to 200 ppm, 80 ppm to 200 ppm, or 80 ppm to 500 ppm). The therapeutic gas can be inhaled in the absence of tobacco smoke.

The therapeutic gas can be inhaled by the mammal continuously over the course of a variety of time periods (e.g., at least 1 minute, at least 2 minutes, at least 3 minutes, at least 4 minutes, at least 5 minutes, at least 6 minutes, at least 7 minutes, at least 8 minutes, at least 9 minutes, or at least 10 minutes). In some embodiments, the therapeutic gas can be inhaled by the mammal continuously over the course of about 7 minutes at a gaseous nitric oxide concentration of about 200 ppm (e.g., when a short inhalation period is required so that a hemoglobin-based oxygen carrier can be administered to a subject, such as a trauma victim, that requires an urgent infusion of an oxygen carrier). In other embodiments, the therapeutic gas can be inhaled by the mammal continuously for at least about 2 minutes, at least about 5 minutes, at least about 15 minutes, at least about 30 minutes, at least about 45 minutes, or at least about 1 hour (e.g., from 2 to 60 minutes, from 2 to 30 minutes, from 2 to 15 minutes, from 5 to 90 minutes, from 5 to 60 minutes, from 5 to 30 minutes, or from 5 to 15 minutes).

In some embodiments of the methods described herein, administration of the nitric oxide-releasing compound or the therapeutic gas is terminated before administration of the composition containing the vasoactive oxygen carrier. In such cases, the mammal is not administered the nitric oxide-releasing compound or the therapeutic gas after the composition has been administered and while the administered vasoactive oxygen carrier is still circulating in the body. In the case of a hemoglobin-based oxygen carrier, by avoiding administration of the nitric oxide-releasing compound or gaseous nitric oxide during the time that the hemoglobin-based oxygen carrier is circulating in the mammal's body, the extent of conversion of the administered hemoglobin to methemoglobin (inactive in oxygen transport) can be minimized. For example, administration of the nitric oxide-releasing compound or the therapeutic gas can be terminated at least one minute (or in some cases at least 2, 3, 4, 5, 10, 15, 30, 45, 60, 90, 120, or 180 minutes) before administration of the composition containing the vasoactive oxygen carrier. In some of these embodiments, administration of the nitric oxide-releasing compound or the therapeutic gas is terminated no more than one minute (or no more than 2, 3, 4, 5, 10, 15, 30, 45, 60, 90, 120, or 180 minutes) before administration of the composition containing the vasoactive oxygen carrier, e.g., immediately before.

In certain embodiments, e.g., in cases of urgency such as when a mammal has suffered severe trauma and time does not permit extensive pretreatment with gaseous nitric oxide, the mammal may continue to inhale the therapeutic gas containing nitric oxide (inhalation of which is commenced prior to administration of a hemoglobin-based oxygen carrier) for a period of time (e.g. about 1, 2, 3, 4, 5, 6, 7, 8, 9, 10, or 15 minutes) after administration of the hemoglobin-based oxygen carrier. In such cases, inhalation of high levels of the therapeutic gas (e.g., 40 ppm or higher) is terminated after a relatively short period of time so as to minimize the extent of conversion of the artificial oxygen carrier present in the patient's blood to a less functional derivative (e.g., in the case of an artificial oxygen carrier that contains hemoglobin, conversion to the inactive molecule methemoglobin (e.g., such that less than about 15%, less than about 10%, or less than about 5% of plasma hemoglobin is converted to methemoglobin)). Alternatively, or in addition, the inhaled gas could contain a low concentration of nitric oxide (e.g., 10 ppm or less) to reduce the conversion of plasma hemoglobin to plasma methemoglobin, thereby permitting an extended inhalation of nitric oxide and optionally multiple transfusions. Examples are described herein demonstrating that nitric oxide can be inhaled, after administration of a hemoglobin-based oxygen carrier, at a low concentration for an extended period of time without extensive conversion of circulating plasma hemoglobin to methemoglobin.

In some embodiments of the methods described herein, the concentration of gaseous nitric oxide in the therapeutic gas is reduced during the course of the administration. In one example, the concentration of gaseous nitric oxide in the therapeutic gas is reduced at a constant rate during all or part of the administration. In another example, the concentration of gaseous nitric oxide in the therapeutic gas is reduced by one or more step-wise reductions during the course of the administration.

Also disclosed are methods of preventing or reducing systemic and pulmonary vasoconstriction in a mammal following administration (single or repeated) of a vasoactive oxygen carrier (e.g., a heme-based oxygen carrier such as a hemoglobin-based oxygen carrier) by: (i) administering to the mammal a first therapeutic gas containing gaseous nitric oxide; (ii) administering to the mammal, during or after administration of the first therapeutic gas, a composition containing a vasoactive oxygen carrier; and (iii) administering to the mammal, after administration of the first therapeutic gas, a second therapeutic gas containing gaseous nitric oxide, wherein the concentration of gaseous nitric oxide in the second therapeutic gas is less than the concentration of gaseous nitric oxide in the first therapeutic gas, and wherein administration of the second therapeutic gas begins (a) after administration of the composition containing the vasoactive oxygen carrier, or (b) before or during administration of the composition containing the vasoactive oxygen carrier and continues after administration of the composition containing the vasoactive oxygen carrier, wherein the first and second therapeutic gases are administered in amounts effective to prevent or reduce the occurrence of systemic and pulmonary vasoconstriction in the mammal following administration of the composition containing the vasoactive oxygen carrier.

Also disclosed are methods of treating an ischemia-reperfusion injury in a mammal by: (i) administering to a mammal that has an ischemia-reperfusion injury a composition containing an oxygen carrier (a vasoactive oxygen carrier or a non-vasoactive oxygen carrier such as a non-vasoactive heme-based oxygen carrier); and (ii) administering to the mammal a therapeutic gas containing gaseous nitric oxide, wherein administration of the therapeutic gas begins (i) before, during, or after administration of the composition comprising the oxygen carrier, or (ii) before or during administration of the composition containing the oxygen carrier and continues after administration of the composition containing the oxygen carrier. The timing and amount of the therapeutic gas administered according to this method can optionally follow the methodology described herein for administration of a second therapeutic gas.

Also disclosed is the use of gaseous nitric oxide for the preparation of first and second therapeutic gases for preventing or reducing the occurrence of vasoconstriction in a mammal following administration of a composition containing a vasoactive oxygen carrier (e.g., a heme-based oxygen carrier such as a hemoglobin-based oxygen carrier) according to the methods described herein.

The first and second therapeutic gases can be administered to the mammal by, for example, inhalation, an artificial lung, or an aqueous solution containing dissolved nitric oxide.

The concentration of gaseous nitric oxide in the first therapeutic gas can be, for example, at least 20 ppm, at least 40 ppm, at least 50 ppm, at least 80 ppm, at least 100 ppm, at least 200 ppm, at least 300 ppm, or at least 500 ppm. In some embodiments, the concentration of gaseous nitric oxide in the first therapeutic gas is in the range of 50 ppm to 500 ppm (e.g., 60 ppm to 200 ppm, 80 ppm to 200 ppm, or 80 ppm to 500 ppm). The first therapeutic gas can be inhaled in the absence of tobacco smoke.

The first therapeutic gas can be inhaled by the mammal continuously over the course of a variety of time periods (e.g., at least 1 minute, at least 2 minutes, at least 3 minutes, at least 4 minutes, at least 5 minutes, at least 6 minutes, at least 7 minutes, at least 8 minutes, at least 9 minutes, or at least 10 minutes). In some embodiments, the first therapeutic gas can be inhaled by the mammal continuously over the course of about 7 minutes at a gaseous nitric oxide concentration of about 200 ppm. In other embodiments, the first therapeutic gas can be inhaled by the mammal (or given by positive pressure mask, via endotracheal intubation, or via injection into the trachea (trans-tracheally) continuously or intermittently (e.g., injected into the commencement of each breath triggered by inhalation)) for at least about 2 minutes, at least about 5 minutes, at least about 15 minutes, at least about 30 minutes, at least about 45 minutes, or at least about 1 hour (e.g., from 2 to 60 minutes, from 2 to 30 minutes, from 2 to 15 minutes, from 5 to 90 minutes, from 5 to 60 minutes, from 5 to 30 minutes, or from 5 to 15 minutes).

The concentration of gaseous nitric oxide in the second therapeutic gas can be, for example, at least 500 ppb, at least 1 ppm, at least 2 ppm, at least 5 ppm, at least 10 ppm, or at least 15 ppm. The concentration of gaseous nitric oxide in the second therapeutic gas can be, for example, less than 40 ppm, less than 30 ppm, less than 25 ppm, or less than 20 ppm. In some embodiments, the concentration of gaseous nitric oxide in the second therapeutic gas is in the range of 500 ppb to 40 ppm (e.g., 1 ppm to 40 ppm, 5 ppm to 40 ppm, 5 ppm to 20 ppm, 5 ppm to 15 ppm, or 5 ppm to 10 ppm). The second therapeutic gas can be inhaled in the absence of tobacco smoke.

The second therapeutic gas can be inhaled by the mammal continuously over the course of a variety of time periods (e.g., at least 3 minutes, at least 15 minutes, at least 1 hour, at least 2 hours, at least 6 hours, at least 12 hours, at least 24 hours, or at least one week or one month).

In some embodiments, the concentration of gaseous nitric oxide in the first therapeutic gas is in the range of 20 ppm to 500 ppm and the concentration of gaseous nitric oxide in the second therapeutic gas is in the range of 500 ppb to 40 ppm.

In some embodiments, administration of the first therapeutic gas is terminated before (at least 3 minutes, at least 15 minutes, or at least 30 minutes before) administration of the composition containing the vasoactive oxygen carrier. In some embodiments, administration of the first therapeutic gas is terminated after administration of the composition containing the vasoactive oxygen carrier.

In some embodiments, administration of the second therapeutic gas begins before or during administration of the composition containing the artificial oxygen carrier and continues after administration of the composition containing the vasoactive oxygen carrier. In some embodiments, administration of the second therapeutic gas begins after administration of the composition containing the vasoactive oxygen carrier.

A single gas delivery device can optionally be used to deliver both the first therapeutic gas and the second therapeutic gas to the mammal, wherein the concentration of administered gaseous nitric oxide is reduced during administration of the first therapeutic gas, thereby resulting in the second therapeutic gas having a concentration of gaseous nitric oxide that is less than the concentration of gaseous nitric oxide in the first therapeutic gas. The concentration of administered gaseous nitric oxide can be reduced at a constant rate subsequent to the initiation of the administration of the first therapeutic gas, thereby resulting in the second therapeutic gas. Alternatively, the concentration of administered gaseous nitric oxide can be reduced by a step-wise reduction subsequent to the initiation of the administration of the first therapeutic gas, thereby resulting in the second therapeutic gas. Nitric oxide-containing gas can be given continuously or injected intermittently at the commencement of each breath (e.g., triggered by each inhalation or thoracic expansion).

In any embodiments of the methods described herein that involve the administration of one or more therapeutic gases to a mammal, the methods can further include a step of administering to the mammal a phosphodiesterase inhibitor (a phosphodiesterase inhibitor described herein such as sildenafil, tadalafil, or vardenafil), a soluble guanylate cyclase sensitizer, or a phosphodiesterase inhibitor and a soluble guanylate cyclase sensitizer. In some embodiments, the phosphodiesterase inhibitor, the soluble guanylate cyclase sensitizer, or the phosphodiesterase inhibitor and the soluble guanylate cyclase sensitizer are administered to the mammal before or after administration of the composition containing the vasoactive oxygen carrier.

Also disclosed are methods of preventing or reducing vasoconstriction in a mammal following administration of a vasoactive oxygen carrier (such as a hemoglobin-based oxygen carrier) by: (i) administering to a mammal a phosphodiesterase inhibitor (e.g., an inhibitor that is selective for cyclic guanosine monophosphate (cGMP) phosphodiesterase) or a soluble guanylate cyclase sensitizer; and (ii) administering to the mammal a composition containing a vasoactive oxygen carrier that (in the absence of the phosphodiesterase inhibitor or soluble guanylate cyclase sensitizer) causes vasoconstriction, wherein the phosphodiesterase inhibitor or the soluble guanylate cyclase sensitizer is administered in an amount effective to prevent or reduce the occurrence of vasoconstriction in the mammal following administration of the composition containing the vasoactive oxygen carrier. The composition containing a vasoactive oxygen carrier can optionally be administered to the mammal during or after administration of the phosphodiesterase inhibitor or the soluble guanylate cyclase sensitizer. This treatment can be carried out in the presence or absence of nitric oxide treatment, e.g., treatment with nitric oxide gas or a nitric oxide-releasing compound as described herein, in the amounts described herein.

Also disclosed is the use of a phosphodiesterase inhibitor or a soluble guanylate cyclase sensitizer for the preparation of a therapeutic composition for preventing or reducing the occurrence of vasoconstriction in a mammal following administration of a composition containing a vasoactive oxygen carrier (e.g., a heme-based oxygen carrier such as a hemoglobin-based oxygen carrier).

Also disclosed is a pharmaceutical composition containing (i) a phosphodiesterase inhibitor (e.g., an inhibitor that is selective for cGMP phosphodiesterase) or a soluble guanylate cyclase sensitizer, and (ii) an artificial oxygen carrier (e.g., a vasoactive artificial oxygen carrier such as a hemoglobin-based oxygen carrier).

A mammal treated according to the methods described herein can be a human (e.g., a Jehovah's witness or a soldier), a non-human primate, or another mammal such as a dog, cat, horse, cow, pig, sheep, goat, rat, mouse, guinea pig, rabbit, or hamster.

A "vasoactive oxygen carrier" is a cell-based (e.g., red blood cells) or cell-free oxygen carrier that is capable of inducing vasoconstriction in at least some of the animals to whom it is administered (when administered in the absence of gaseous nitric oxide).

Red blood cells can be derived from an autologous or allogeneic donor prior to transfusion to a mammal. In some embodiments, red blood cells are stored (e.g., for at least 1, 2, 3, 4, 5, 6, or 12 hours or at least 1, 2, 3, 4, 5, 6, 7, 14, 21, or 28 days) after removal from a donor and prior to administration to the mammal An "artificial oxygen carrier" is a cell-free vasoactive oxygen carrier.

A "heme-based oxygen carrier" is a cell-free artificial oxygen carrier that contains heme (in combination with a heme-carrying molecule such as globin, albumin, or dextran) and is capable of delivering oxygen to tissues. Heme-based oxygen carriers include heme-albumin-based oxygen carriers, heme-dextran-based oxygen carriers, and hemoglobin-based oxygen carriers.

A "hemoglobin-based oxygen carrier" is a cell-free artificial oxygen carrier that contains native or modified hemoglobin and is capable of delivering oxygen to tissues. The hemoglobin-based oxygen carrier can contain a native hemoglobin (e.g., native human, bovine, or porcine hemoglobin) or a modified hemoglobin (e.g., a modified human, bovine, or porcine hemoglobin, such as modified by pegylation with polyethylene glycol). The hemoglobin-based oxygen carrier can contain, for example, cross-linked hemoglobin (e.g., cross-linked tetrameric hemoglobin), cross-linked polyhemoglobin, conjugated hemoglobin, recombinant hemoglobin, or encapsulated hemoglobin. The hemoglobin-based oxygen carrier can be administered to a mammal by, e.g., intravenous, intraarterial, or intraosseous infusion.

Vasoactive oxygen carriers (e.g., hemoglobin-based oxygen carriers) can be administered to a mammal by the methods described herein for essentially any purpose in which blood transfusions are typically given. For example, a mammal treated according to the methods described herein may have an anemia (e.g., severe acute anemia or sickle cell anemia), may have suffered blood loss (e.g., as a result of trauma or a surgical procedure such as cardiac or orthopedic surgery), and/or may be a Jehovah's Witness and refuse human blood transfusion.

Vasoactive oxygen carriers (e.g., hemoglobin-based oxygen carriers) can also be administered to a mammal before, during, and/or after the occurrence of an ischemic event so as to increase the plasma oxygen content and thereby oxygenate ischemic tissue preventing ischemic cell damage (and protecting the tissue from reperfusion injury). For example, a vasoactive oxygen carrier (e.g., a heme-based oxygen carrier such as a hemoglobin-based oxygen carrier) can be administered to a mammal (in combination with and/or following e.g., inhalation of gaseous nitric oxide) to provide protection (e.g., myocardial protection) due to acute ischemia and subsequent reperfusion and free radical release caused by, e.g., surgical revascularization (e.g., percutaneous coronary revascularization), transplantation, acute myocardial infarction, or angioplasty (e.g., percutaneous coronary angioplasty). A mammal treated according to the methods described herein may have ischemic heart disease, may have suffered an acute ischemic event (e.g., myocardial infarction, stroke, or renal ischemia), or may exhibit vasospasm of an organ (e.g., the brain, heart, kidney, liver, or an organ of the gastrointestinal tract) prior to treatment. Administration of gaseous nitric oxide or a nitric oxide-releasing compound according to the methods described herein can enhance (via vasodilation) the availability of plasma oxygen carried by an oxygen carrier far smaller than red blood cells to an ischemic tissue (e.g., heart or brain) until angioplasty or thrombolysis occurs.

Also disclosed is a gas-delivery device containing: (i) a lumen configured to route a gas into the respiratory system of a mammal; (ii) a first meter configured to measure the concentration of nitric oxide in the gas present in the lumen; (iii) a second meter configured to measure the rate of gas flow in the lumen; and (iv) a dosimeter that integrates the concentration of nitric oxide measured in the lumen with the rate of gas flow measured in the lumen to determine the total cumulative amount of nitric oxide delivered by the device (less the net expired gas) to the respiratory system of the mammal at any given moment in time. In some embodiments, the device also includes a vessel containing pressurized gas containing at least 1 ppm (e.g., at least 20 ppm) nitric oxide, wherein the vessel has a mechanism for controllably releasing the gas into the lumen or into a chamber in communication with the lumen. In other embodiments, the release of pressurized nitric oxide-containing gas is triggered by the negative inspiratory pressure of the patient, and the gas release is limited to the inspiratory cycle of respiration, thereby reducing the delivery of inspired gas to the respiratory dead space and reducing the requirement for inspired gas, conserving a possibly limited supply.

Also disclosed is a kit containing (i) a first vessel containing pressurized gas containing at least 1 ppm nitric oxide (e.g., at least 20 ppm), and (ii) a second vessel containing a composition containing an artificial oxygen carrier (e.g., a vasoactive oxygen carrier such as a hemoglobin-based oxygen carrier).

Also disclosed is a kit containing (i) a gaseous nitric oxide delivery device (e.g., as described herein), and (ii) a composition containing an artificial oxygen carrier (e.g., a vasoactive oxygen carrier such as a hemoglobin-based oxygen carrier). In some embodiments, the kit also includes a vessel containing pressurized gas containing at least 1 ppm nitric oxide (e.g., at least 20 ppm). The kit can optionally be configured to permit (e.g., via operation of a switch) delivery of nitric oxide initially at a concentration described herein for treatment with a first therapeutic gas (e.g., in the range of 20 ppm to 500 ppm) and subsequently at a concentration described herein for treatment with a second therapeutic gas (e.g., in the range of 500 ppb to 40 ppm).

Also disclosed is a kit containing (i) a phosphodiesterase inhibitor (e.g., an inhibitor that is selective for cGMP phosphodiesterase) or a soluble guanylate cyclase sensitizer, and (ii) a composition containing an artificial oxygen carrier (e.g., a vasoactive oxygen carrier such as a hemoglobin-based oxygen carrier).

Certain methods described herein allow for prevention or reduction in the occurrence of vasoconstriction in a mammal following administration of an artificial oxygen carrier (e.g., a heme-based oxygen carrier such as a hemoglobin-based oxygen carrier). It has been surprisingly found that by inhaling nitric oxide prior to administration of a hemoglobin-based oxygen carrier, conversion of (active) ferrous-heme-containing hemoglobin to (inactive) ferric-heme-containing methemoglobin is substantially minimized (as compared to the substantial conversion of plasma hemoglobin to methemoglobin that accompanies extended concurrent inhalation of nitric oxide and administration of a hemoglobin-based oxygen carrier). Furthermore, it has also been surprisingly found that inhalation of nitric oxide at a low concentration subsequent to administration of a hemoglobin-based oxygen carrier can prevent or reduce the occurrence of pulmonary vasoconstriction (and is expected to prevent future vasoconstriction with infusion of one or more additional units of oxygen carrier) without causing significant conversion of the administered hemoglobin to inactive methemoglobin.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control. Suitable methods and materials are described below, although methods and materials similar or equivalent to those described herein can also be used in the practice or testing of the present invention. The materials, methods, and examples are illustrative only and not intended to be limiting.

Other features and advantages of the invention will be apparent from the following detailed description, and from the claims.

DETAILED DESCRIPTION

Figure 1:
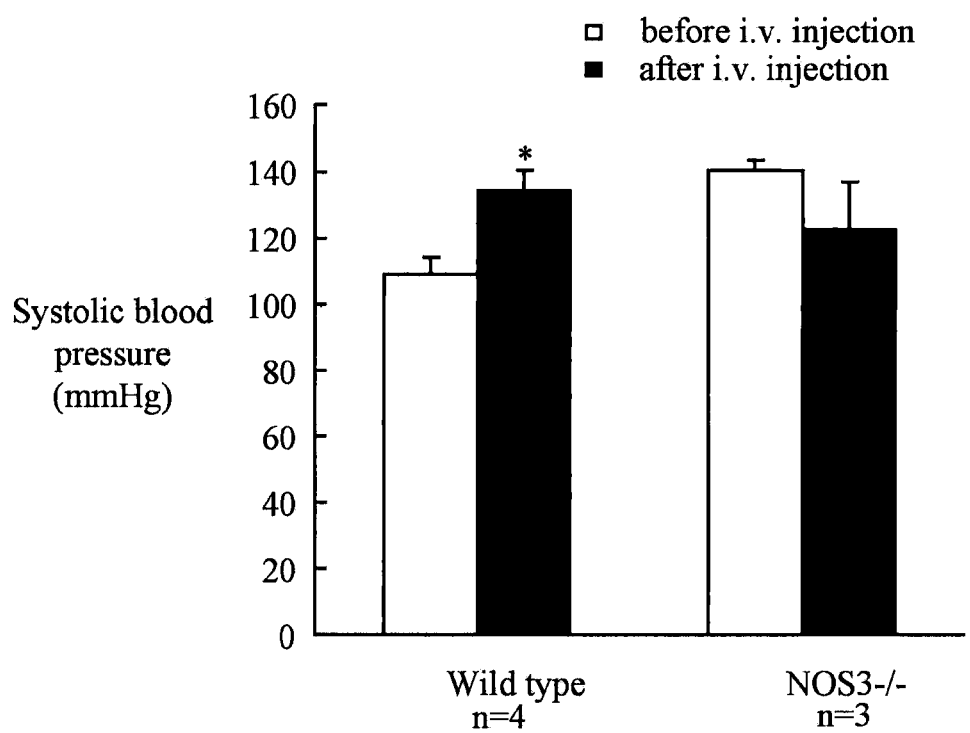
FIG. 1 is a graph depicting tail systolic blood pressure in awake wild type mice and NOS3−/− mice before and after intravenous injection of murine tetrameric hemoglobin solution.

Systemic and pulmonary vasoconstriction often follows administration of an oxygen carrier (e.g., a heme-based oxygen carrier such as a hemoglobin-based oxygen carrier) to a mammal. The present invention provides compositions and methods for preventing or reducing such oxygen carrier-induced vasoconstriction. As detailed in the accompanying examples, inhalation of nitric oxide prior to administering a heme-based oxygen carrier to a mammal, optionally coupled with continued inhalation of nitric oxide at a low concentration subsequent to administration of the heme-based oxygen carrier, can prevent or reduce the occurrence of vasoconstriction in the mammal without causing significant conversion of the administered active ferrous heme to inactive ferric heme.

Vasoactive Oxygen Carriers

Vasoactive oxygen carriers used according to the methods described herein include red blood cells that are derived from an autologous or allogeneic donor and subsequently administered to a recipient. Short or long term storage of red blood cells results in depletion of nitric oxide (and/or nitric oxide carrier) levels in the stored blood, which depletion results in an induction of vasoconstriction following administration of the stored blood to a recipient (Reynolds et al. (2007) *Proc. Natl. Acad. Sci.* 104:17058-62; Bennett-Guerrero et al. (2007) *Proc. Natl. Acad. Sci.* 104:17063-68). Red blood cells can be stored for a variety of time periods (e.g., at least 1, 2, 3, 4, 5, 6, or 12 hours or at least 1, 2, 3, 4, 5, 6, 7, 14, 21, or 28 days) prior to transfusion to a donor according to the methods described herein. Red blood cells can be administered as, e.g., whole blood or packed red blood cells.

As an alternative to red blood cells, vasoactive oxygen carriers used in the methods described herein can be artificial oxygen carriers such as heme-based oxygen carriers. Heme-based oxygen carriers contain heme in combination with a heme carrying molecule such as globin (i.e., a hemoglobin-based oxygen carrier), albumin, or dextran.

A hemoglobin-based oxygen carrier can contain hemoglobin that is native (unmodified), hemoglobin that is modified by genetic engineering, and/or hemoglobin that is modified by a chemical reaction such as intra- or inter-molecular cross-linking, polymerization, or the addition of chemical groups (e.g., polyalkylene oxides, polyethylene glycol, superoxide dismutase or other adducts).

Chemical cross-linking of a hemoglobin tetramer can involve, for example, binding of the hemoglobin alpha subunits by a bifunctional agent (e.g., diaspirin) that links the hemoglobin molecules and thus stabilizes them. Alternatively, hemoglobin tetramer cross-linking can be achieved by genetic modification of native hemoglobin (the structure and amino acid sequence of which is known). For example, by the addition of a single amino acid it is possible to covalently bind two alpha subunits and thereby prevent dissociation of the hemoglobin tetramer. Insertion of an engineered hemoglobin into a plasmid for expression in *E. coli* can permit the production of large quantities of hemoglobin.

The hemoglobin component of a hemoglobin-based oxygen carrier can be derived from human or non-human sources (e.g., mammals such as cows, pigs, or horses or non-mammalian sources such as annelids and reptiles). Examples of modified hemoglobin include cross-linked polyhemoglobin, cross-linked tetrameric hemoglobin, conjugated hemoglobin, recombinant hemoglobin, and encapsulated hemoglobin.

Several hemoglobin-based oxygen carriers are commercially available and include, e.g., Hemopure® (HBOC-201; a chemically cross-linked bovine hemoglobin formulated in a salt solution; Biopure, Cambridge, Mass.), PolyHeme® (a solution of a chemically polymerized form of human hemoglobin; Northfield Laboratories Inc., Evanston, Ill.), Oxyglobin® (HBOC-301; a bovine hemoglobin glutamer approved for veterinary use; Biopure, Cambridge, Mass.), and Hemolink™ (a hemoglobin raffimer; Hemosol Inc., Mississauga, Ontario). Others are discussed in Winslow (2003) *J Intern Med.* 253:508; Vandegriff et al. (2003) *Transfusion* 43:509; and Bjorkholm et al. (2005) *Haematologica* 90:505. Artificial oxygen carriers that are not hemoglobin-based are mentioned in Winslow (2003) *J Intern Med.* 253:508. Determination of whether any given oxygen carrier is vasoactive (i.e., capable of constricting blood vessels) can be carried out by administering the oxygen carrier to an animal and measuring resulting vasoconstriction by any appropriate technique. In an animal with normal (i.e., not depleted) blood volume, vasoconstriction can be suggested as a function of blood pressure (see, e.g., Winslow (2003) at pages 508-509).

A pharmaceutical composition can be formulated, for example, by mixing a vasoactive oxygen carrier, one or more excipients, and/or one or more diluents. The following are examples of clinical settings in which a composition containing a vasoactive oxygen carrier can be administered (e.g., via intravenous, intraarterial, or intraosseous infusion) to a mammal: trauma or hemorrhage (e.g., an acute loss of whole blood); ischemia (conditions resulting in ischemia include heart attack, stroke, and cerebrovascular trauma); hemodilution (blood is removed pre-operatively, e.g., to permit use of autologous blood rather than allogeneic transfusions post-operatively); to act as a priming solution in cardiopulmonary bypass; septic shock; and anemia (e.g., chronic anemia or sickle cell anemia). In the treatment of ischemia, gaseous nitric oxide can optionally be inhaled during an ischemic period (e.g., before percutaneous coronary angioplasty) and a vasoactive oxygen carrier can then be infused thereafter. The small size of a heme-based oxygen carrier would generally allow it to perfuse retrograde and through partially blocked vessels, thereby carrying oxygen to the ischemic area and minimizing injury. Heme-based oxygen carriers can also be used in the treatment of non-humans, e.g., in the emergency treatment of domestic and wild animals suffering a loss of blood due to injury or anemia.

The preparation and use of heme-based oxygen carriers are reviewed in detail in, e.g., Spahn et al. (2005) *Curr Pharm Des.* 11(31):4099, Greenburg et al. (2004) *Crit. Care.* 8 Suppl 2:S61, and *Artificial Oxygen Carrier: Its Front Line* (Koichi Kobayashi et al. eds., 2005).

Administration of Gaseous Nitric Oxide

Administration of a vasoactive oxygen carrier (e.g., a heme-based oxygen carrier such as a hemoglobin-based oxygen carrier) can result in the induction of systemic and pulmonary vasoconstriction in the recipient. As detailed herein, inhalation of gaseous nitric oxide prior to and optionally subsequent to vasoactive oxygen carrier administration can prevent or reduce the occurrence of vasoconstriction that otherwise occurs following administration of the artificial oxygen carrier.

Methods for safe and effective administration of nitric oxide are described in, e.g., Zapol, U.S. Pat. No. 5,570,683; Zapol et al., U.S. Pat. No. 5,904,938; Bach et al., U.S. Published Application No. 20030039638; Higenbottam, U.S. Pat. No. 5,839,433; and Frostell et al. (1991) *Circulation* 83:2038. Pharmaceutical grade nitric oxide for inhalation is available commercially (INOmax™, INO Therapeutics, Inc., Clinton, N.J.).

A subject can inhale a pre-determined concentration or total amount of gaseous nitric oxide prior to and/or subsequent to administration of a vasoactive oxygen carrier. A suitable concentration of nitric oxide administered by inhalation prior to administration of a vasoactive oxygen carrier can vary, e.g., from 20 ppm to 80 ppm, 200 ppm to 500 ppm, or higher, depending on the age and condition of the patient, the length of the inhalation period, the disease or disorder being treated, the amount of vasoactive oxygen carrier to be administered, whether a compound such as a phosphodiesterase inhibitor and/or a soluble guanylate cyclase sensitizer is also administered to the patient (in which case a reduced concentration of nitric oxide can be used), and/or other factors that a treating physician may deem relevant. A suitable concentration of nitric oxide administered by inhalation subsequent to administration of a vasoactive oxygen carrier can also vary, e.g., from 2 to 40 ppm or 5 to 10 ppm, based upon the factors described above. Preferably, the lowest effective dose is inhaled. Continued, extended low dose inhalation of nitric oxide (e.g., for hours or days, as detailed herein) according to the methods described herein permits multiple infusions of a vasoactive oxygen carrier (e.g., autologous blood transfusion or a heme-based oxygen carrier such as a hemoglobin-based oxygen carrier) to be given to a mammal over an extended period of time. Low dose nitric oxide inhalation can continue for a variety of time periods (including but not limited to at least 1, 2, 3, 4, 5, 6, or 12 hours or at least 1, 2, 3, 4, 5, 6, or 7 days), during which period the mammal receives multiple infusions of the vasoactive oxygen carrier.

Gaseous nitric oxide can be administered by inhalation from a source of stored, compressed nitric oxide gas. The source of nitric oxide can be 100% nitric oxide, or diluted with $N_2$ or any other inert gas (e.g., helium). The nitric oxide can be obtained and stored as a mixture free of any contaminating $O_2$ or higher oxides of nitrogen, because such higher oxides of nitrogen (which can form by reaction of $O_2$ with nitric oxide) are potentially harmful to lung tissues. If desired, purity of the nitric oxide may be demonstrated with chemiluminescence analysis, prior to administration to a patient. Chemiluminescence NO—$NO_x$ analyzers are commercially available (e.g., Model 14A, Thermo Environmental Instruments, Franklin, Mass.). The NO—$N_2$ mixture may be blended with $O_2$ or an $O_2$-containing gas such as air through, for example, calibrated rotameters which have been validated previously with a spirometer. The final concentration of nitric oxide in the breathing mixture may be verified with a chemical or chemiluminescence technique (see, e.g., Fontijn et al., Anal. Chem. 42:575 (1970)). Alternatively, NO and $NO_2$ concentrations may be monitored by means of an electrochemical analyzer. Any impurities such as $NO_2$ can be scrubbed by exposure to NaOH solutions, baralyme, or sodalime. As an additional control, the $FiO_2$ of the final gas mixture may also be assessed. If desired, the ventilator may have a gas scavenger added to the expiratory outlet to ensure that significant amounts of NO will not escape into the adjacent environment.

In a hospital or emergency field situation, administration of nitric oxide gas could be accomplished, for example, by attaching a tank of compressed nitric oxide gas in $N_2$, and a second tank of oxygen or an oxygen/$N_2$ mixture, to an inhaler designed to mix gas from two sources. By controlling the flow of gas from each source, such as with the device illustrated in FIG. 9, the concentration of nitric oxide inhaled by the patient can be maintained at an optimal level. Nitric oxide gas may also be mixed with room air, using a standard low-flow blender (e.g., Bird Blender, Palm Springs, Calif.). Nitric oxide may be generated from $N_2$ and $O_2$ (i.e., air) by using an electric nitric oxide generator. Such a generator is described in Zapol, U.S. Pat. No. 5,396,882. Portable nitric oxide delivery devices can be used in the field (e.g., by military paramedics or by ambulance personnel) to permit infusion of vasoactive oxygen carriers such as hemoglobin-based oxygen carriers (during or after gaseous nitric oxide inhalation) in the critical early periods following trauma or hemorrhage.

A gas delivery device (e.g., a portable device for field use) for nitric oxide delivery can contain a nitric oxide dosimeter to permit the monitoring of the total dose of nitric oxide administered to a subject. By use of a dosimeter, a determination can be made of when a subject has received the required amount of nitric oxide so that administration of the nitric oxide can be tapered off or terminated and administration of the vasoactive oxygen carrier (e.g., a heme-based oxygen carrier such as a hemoglobin-based oxygen carrier) can begin. Monitoring the total cumulative inhaled dose permits one to minimize the delay in the administration of a vasoactive oxygen carrier to the patient. This can be crucial in certain situations, such as when a subject has suffered trauma or hemorrhage (e.g., a soldier on the battlefield) and requires administration of a vasoactive oxygen carrier as soon as is possible.

Figure 9:
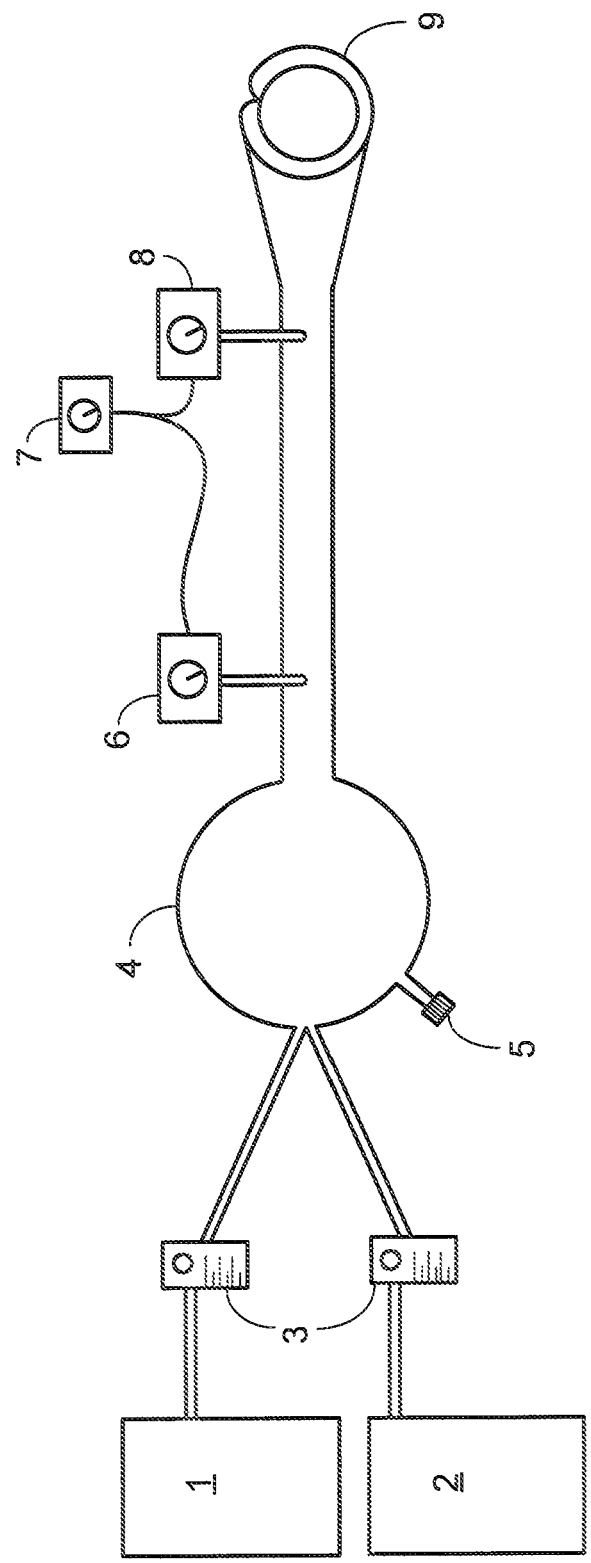
FIG. 9 is a schematic drawing of a nitric oxide dosimeter-containing gas delivery device.

A dosimeter can integrate the concentration of nitric oxide in the therapeutic gas (as measured by a nitric oxide concentration meter) with the gas flow rate (as measured by a gas flow meter) or the number of inhalations to determine the total amount of nitric oxide administered to a subject (FIG. 9). A delivery device containing such a dosimeter can be used for pre-dosing the subject so that a predetermined amount of nitric oxide is administered and absorbed. As detailed in the accompanying Examples, 7 minutes of breathing 200 ppm nitric oxide is sufficient to prevent vasoconstriction in a mouse to which a tetrameric hemoglobin solution is subsequently administered. If this can be directly scaled up to a human, one example of the number of inhaled moles of nitric oxide sufficient to prevent vasoconstriction in a 70 kg human can be estimated as follows (based upon 7 minutes of breathing 200 ppm nitric oxide): (i) (7 minutes)×(10 breaths per minute) is 70 breaths; (ii) since a breath in a human is approximately one liter, 70 breaths would be 70 liters of 200 ppm nitric oxide; (iii) of each breath, approximately half is absorbed and half is exhaled in dead space; (iv) 35 liters of 200 ppm nitric oxide results in absorption of 0.312 millimoles of nitric oxide for a 70 kg adult.

FIG. 9 is a schematic drawing of a nitric oxide dosimeter-containing gas delivery device containing the following components: $O_2$ cylinder (1); NO cylinder (2); gas flow rotameters (3); reservoir (4); pop-off valve set at 5 cm $H_2O$ pressure (5); NO concentration meter (6) integrating NO dosimeter (7); gas flowmeter (8); and face mask (9). The nitric oxide dosimeter-containing device depicted in FIG. 9 is merely an example and can be modified in a variety of ways without loss of functionality. For example, the nitric oxide cylinder could instead be an NO/$N_2$ cylinder or an NO/helium cylinder. Because 20 to 500 breaths of 200 to 300 ppm nitric oxide may provide a sufficient dose to treat certain subjects in the field, the nitric oxide containing cylinder could be quite small, particularly if the concentration of nitric oxide in the cylinder is relatively high (e.g., 5,000 to 50,000 ppm nitric oxide in a diluent such as $N_2$). In addition, if a high concentration of nitric oxide is used for a short period of time, supplemental $O_2$ may not be required and in fact may be preferentially omitted (the $O_2$ cylinder is thus optional). The gas flowmeter can be used, for example, to vary the dose of nitric oxide administered such that a high dose is provided early in the loading and a low dose is provided later to avoid methemoglobin production (in those instances where a hemoglobin-based oxygen carrier is administered). A reduction over time in the amount of nitric oxide administered to a subject can be achieved in a variety of ways. For example, the amount of nitric oxide administered to a subject can be reduced by a one or multi-step reduction in the concentration of the nitric oxide to be inhaled (e.g., reducing the concentration of inhaled nitric oxide from 80 ppm to 5 ppm in a single step) or a continuous decline in the concentration of nitric oxide to be inhaled (e.g., reducing the concentration of inhaled nitric oxide from 80 ppm to 5 ppm at a constant rate of decline over an extended period of time). Such reductions in nitric oxide concentration can be effectuated manually by an operator of a nitric oxide delivery device or automatically by a machine programmed to control the reduction.

In addition to containing a dosimeter to measure (and optionally control) the amount of nitric oxide administered, an inhaler device may also be configured to measure the amount of nitric oxide exhaled by a subject, so as to permit the measurement of the actual amount of nitric oxide that is absorbed. By subtracting the amount of nitric oxide exhaled by the subject from the amount of nitric oxide administered (as measured by the dosimeter), a measurement of the actual amount absorbed can be obtained. As above, this measurement can be used to determine the earliest possible time subsequent to the initiation of nitric oxide inhalation at which the required cumulative dose has been administered and thus it is acceptable to proceed with administration of a vasoactive oxygen carrier to the subject. Methods and devices for measuring the amount of nitric oxide in exhaled air are described in, e.g., Steerenberg et al. (2004) Methods Mol Biol. 279:45, Grasemann et al. (2004) Pediatr Pulmonol. 38(5):379, and Spahn et al. (2006) Ann Allergy Asthma Immunol. 96(4):541.

Gaseous nitric oxide can optionally be administered via inhalation by nasal prongs, face mask, tent, intra-tracheal catheter or endotracheal tube, for an extended period, e.g., minutes, hours, or days. The administration may be continuous during the extended period. Alternatively, administration could be intermittent during the extended period (e.g., nitric oxide injected only in the initial portion of each inspiration (sensed by triggering after the inspiratory negative pressure waveform), or is present only in every third inhalation, or for only ten minutes every hour for several hours). The administration of gaseous nitric oxide may be via spontaneous or mechanical ventilation.

An artificial lung (a catheter device for gas exchange in the blood) designed for $O_2$ delivery and $CO_2$ removal can be used for nitric oxide delivery. The catheter, when implanted, resides in one of the large veins and would be able to deliver nitric oxide at given concentrations either for systemic delivery or at a local site. The delivery can be a local delivery of a high concentration of nitric oxide for a short period of time at a specific site (this high concentration would rapidly be diluted out in the bloodstream) or a relatively longer systemic exposure to a lower concentration of nitric oxide (see, e.g., Hattler et al. (1994) Artif. Organs 18(11):806; and Golob et al. (2001) ASAIO J. 47(5):432). The nitric oxide can be mixed with $O_2$ (just prior to delivery, to minimize oxidation of the nitric oxide) and/or an inert gas such as $N_2$.

A whole patient can be exposed to nitric oxide. A patient can be placed inside an airtight chamber that is flooded with nitric oxide (at a level that does not endanger the patient, or at a level that poses an acceptable risk without the risk of bystanders being exposed). Upon completion of the exposure, the chamber could be flushed with air (e.g., 21% $O_2$, 79% $N_2$).

Aqueous solutions containing nitric oxide can be created for systemic delivery to a patient, e.g., for oral delivery and/or by injection into the body, e.g., intravenously, intra-arterially, intraperitoneally and/or subcutaneously.

Nitric oxide administration (e.g., by inhalation) can be terminated prior to administration of a vasoactive oxygen carrier (e.g., a heme-based oxygen carrier such as a hemoglobin-based oxygen carrier), concurrent with the administration, or shortly after the administration. Although extended administration of nitric oxide at higher levels subsequent to administration of a hemoglobin-based oxygen carrier may result in significant conversion of hemoglobin to inactive methemoglobin and is therefore generally undesirable, continuing nitric oxide administration for a short period (no more than, e.g., 30 seconds, 1 minute, 5 minutes, 10 minutes, or 15 minutes) and/or at a low concentration subsequent to administration of the hemoglobin-based oxygen carrier may be acceptable if it does not result in excessive conversion of the administered hemoglobin to inactive methemoglobin (e.g., at the peak, less than 5%, 10%, or 15% total plasma hemoglobin is methemoglobin). If significant methemoglobin levels are produced, they can be reverted to oxyhemoglobin by infusing an electron donor such as methylene blue or ascorbic acid. If administration of nitric oxide is continued after administration of a heme-based oxygen carrier, the acceptable duration of this continued administration may depend upon the need for further oxygen carrier transfusions, the concentration of nitric oxide administered (usually less than 40 ppm if for an extended period of time after administration of the heme-based oxygen carrier), the duration of the nitric oxide administration prior to heme-based oxygen carrier administration, the amount of heme-based oxygen carrier administered, and/or the circulating lifespan of the heme-based oxygen carrier in the plasma and perivascular interstitial spaces.

Nitric Oxide-Releasing Compounds

As an alternative (or in addition to) to administration of gaseous nitric oxide, a nitric oxide-releasing compound can be administered to a subject according to the methods described herein. Nitric oxide-releasing compounds useful in the methods described herein include: nitroso or nitrosyl compounds (e.g., S-nitroso-N-acetylpenicillamine, S-nitroso-L-cysteine, and nitrosoguanidine) characterized by a nitric oxide moiety that is spontaneously released or otherwise transferred from the compound under physiological conditions such as obtain in the lung; compounds in which nitric oxide is a ligand on a transition metal complex, and as such is readily released or transferred from the compound under physiological conditions (e.g., nitroprusside, nitric oxide-ferredoxin, or a nitric oxide-heme complex); and nitrogen-containing compounds that are metabolized by enzymes endogenous to the respiratory and/or vascular system to produce the nitric oxide radical (e.g., arginine, glyceryl trinitrate, isoamyl nitrite, sodium nitrite, inorganic nitrite, azide, and hydroxylamine). Additional nitric oxide-releasing compounds include nitroglycerin and SIN-1.

The nitric oxide-releasing compound can be an ultra-short-acting nitric oxide-releasing compound such as 1-hydroxy-2-oxo-3-(N-methyl-3-aminopropyl)-3-methyl-1-triazene ("NOC-7"; Zhang et al. (1996) Circulation 94:2235) or a nitric oxide adduct of N,N'-dimethylhexanediamine ("DMHD/NO"; Kaul et al. (1997) J. Cardiovasc. Pharmacol. Ther. 1997 2(3):181). In some embodiments, the ultra-short-acting nitric oxide-releasing compound has a half life of less than 90 minutes (or less than 60 minutes, less than 30 minutes, less than 20 minutes, less than 10 minutes, less than 5 minutes, less than 2 minutes, or less than 1 minute).

A compound known or believed to be a nitric oxide-releasing compound (e.g., an ultra-short-acting nitric oxide-releasing compound) can be directly tested for its efficacy by use of an animal model described herein. Alternatively, such a compound may first be screened for its ability to stimulate guanylate cyclase, the enzyme to which nitric oxide binds and thereby exerts its biological activity, in an in vitro assay such as is described by Ishii et al. (1991) Am. J. Physiol. 261: H598-H603.

Assessment of Effects of Administered Nitric Oxide or Nitric Oxide-Releasing Compound When gaseous nitric oxide (or a nitric oxide-releasing compound) and a vasoactive oxygen carrier (e.g., a heme-based oxygen carrier such as a hemoglobin-based oxygen carrier) are administered to a subject, it may be desirable to monitor the effects of the administrations. Such monitoring can be used to verify the effects of the treatment in a particular individual. Such monitoring can also be useful in adjusting dose level, duration, and frequency of administration of nitric oxide (or nitric oxide-releasing compound) and/or vasoactive oxygen carrier (e.g., hemoglobin-based oxygen carrier) in a given individual.

The effects of administration of gaseous nitric oxide (or a nitric oxide-releasing compound) on vasoactive oxygen carrier (e.g., a heme-based oxygen carrier such as a hemoglobin-based oxygen carrier)-induced vasoconstriction can be assessed by standard medical analyses. For example, systemic blood pressure can be monitored by an arterial line or a blood pressure cuff and pulmonary artery pressure can be monitored via a flow-directed pulmonary artery catheter, cardiac ultrasound, or range-gated doppler techniques. In addition, cardiac ischemia can be monitored via an electrocardiogram.

In those embodiments where a hemoglobin-based oxygen carrier is administered, the effects of administration of nitric oxide (or a nitric oxide-releasing compound) on conversion of administered hemoglobin to methemoglobin or ferrous heme to ferric heme (inactive in oxygen transport) can also be monitored. Hemoglobin and methemoglobin concentration in whole blood and plasma can be determined, for example, by the cyanomethemoglobin method. See, e.g., Matsuoka (1977) *Biol. Pharm. Bull.* 20(11):1208-11. "Plasma hemoglobin and methemoglobin concentration" refers to the concentration of hemoglobin and methemoglobin in the cell-free fraction of the blood (and includes hemoglobin present in a hemoglobin-based oxygen carrier, if administered).

Other Agents

A phosphodiesterase inhibitor can be administered in conjunction with nitric oxide or a nitric oxide-releasing compound to inhibit the breakdown of cGMP by endogenous phosphodiesterases (see, e.g., U.S. Pat. Nos. 5,570,683 and 5,823,180). In addition, or alternatively, a compound that sensitizes soluble guanylate cyclase to nitric oxide can be co-administered (see, e.g., WO 2005/077005 and WO 2006/037491). These compounds can be used, for example, to enhance the effectiveness of nitric oxide inhalation and/or to reduce the amount of nitric oxide inhaled (for example, a therapeutic gas containing a reduced nitric oxide concentration, e.g., in the range of 1 or 250 ppb to 40 ppm, can be inhaled in certain instances when a phosphodiesterase inhibitor and/or a soluble guanylate cyclase sensitizer is administered to a subject).

A phosphodiesterase inhibitor and/or soluble guanylate cyclase sensitizer can alternatively be administered in combination with a vasoactive oxygen carrier (e.g., a heme-based oxygen carrier such as a hemoglobin-based oxygen carrier) without co-administration of nitric oxide or a nitric oxide-releasing compound.

A phosphodiesterase inhibitor and/or soluble guanylate cyclase sensitizer can be introduced into a subject by any suitable method, including via an oral, transmucosal, intravenous, intramuscular, subcutaneous, or intraperitoneal route. The compounds can also be inhaled by the subject.

Examples of phosphodiesterase inhibitors include: Zaprinast® (M&B 22948; 2-o-propoxyphenyl-8-azapurine-6-one; Rhone-Poulenc Rorer, Dagenham Essex, UK); WIN 58237 (1-cyclopentyl-3-methyl-6-(4-pyridyl)pyrazolo[3,4-d]pyrimidin-4-(5H)-one; Silver et al. (1994) J. Pharmacol. Exp. Ther. 271:1143); SCH 48936 ((+)-6a,7,8,9,9a,10,11,11a-octahydro-2,5-dimethyl-3H-pentalen(6a,1,4,5)imidazo[2,1-b]purin-4(5H)-one; Chatterjee et al. (1994) Circulation 90:1627, abstract no. 3375); KT2-734 (2-phenyl-8-ethoxycycloheptimidazole; Satake et al. (1994) Eur. J. Pharmacol. 251:1); E4021 (sodium 1-[6-chloro-4-(3,4-methylenedioxybenzyl)-aminoquinazolin-2-y]piperidine-4-carboxylate sesquihydrate; Saeki et al. (1995) J. Pharmacol. Exp. Ther. 272:825); sildenafil (Viagra®); tadalafil (Clalis®); and vardenafil (Levitra®).

Examples of compounds that sensitize soluble guanylate cyclase include: 3-(5'-hydroxymethyl-2'-furyl)-1-benzylindazole ("YC-1"; Russwurm (2002) J. Biol. Chem. 277:24883; Schmidt et al. (2001) Mol. Pharmacol. 59:220; and Friebe et al. (1998) Mol. Pharmacol. 54:962); compounds loosely based on YC-1 such as the pyrazolopyridine BAY 41-2272 (Stasch et al. (2001) Nature 410:212), the BAY 41-2272 derivatives ortho-(BAY 50-6038), meta-(BAY 51-9491) and para-PAL-(BAY 50-8364) (Becker et al. (2001) BMC Pharmacol. 1:13), and BAY 41-8543 (Stasch et al. (2002) Brit. J. Pharmacol. 135:333); 2-[1-(2-fluorobenzyl)-1H-pyrazolo[3,4-b]pyridin-3-yl]-5-(4-morpholinyl)-4,6-pyrimidine-diamine; 2-[1-(2-fluorobenzyl)-1H-pyrazolo[3,4-b]pyridin-3-yl]-5-(4-pyridinyl)-4-pyrimidmamine; methyl-4,6-diamino-2-[1-(2-fluorobenzyl)-1H-pyrazolo[3,4-b]pyridin-3-yl]-5-pyrimidinyl-(methyl)carbamate; methyl-4,6-diamino-2-[1-(2-fluorobenzyl)-1H-pyrazolo[3,4-b]pyridin-3-yl]-5-pyrimidinyl-carbamate; and 4-[((4-carboxybutyl)-{2-[(4-phenethylbenzyl)oxy]phenethyl}amino)methyl]benzoic acid.

The following are examples of the practice of the invention. They are not to be construed as limiting the scope of the invention in any way.

EXAMPLES

Example 1

Nitric Oxide-Dependent Increase in Blood Pressure Following Infusion of Tetrameric Hemoglobin Solution Nitric oxide synthase 3 (NOS3) is expressed in pulmonary vascular endothelial cells and participates in the control of pulmonary vascular tone by synthesizing nitric oxide, which stimulates vascular smooth muscle cGMP synthesis and causes vasorelaxation. NOS3 deficient mice (NOS3−/−) exhibit systemic and pulmonary hypertension under normoxic conditions (Huang et al. (1995) Nature 377:239; and Steudel et al. (1997) Circ. Res. 81:34).

Animal Preparation 8 to 10 week old male C57BL/6 wild type mice and male NOS3-deficient mice (B6129P2-NOS3$^{tm1/Unc}$; NOS3$^{−/−}$), which were backcrossed 10 generations onto a C57BL/6 background, were studied. All mice were obtained from the Jackson Laboratory (Bar Harbor, Me.) and maintained in the Massachusetts General Hospital's animal resource facility.

Preparation of Murine Tetrameric Hemoglobin Solution

Murine whole blood from wild type C57BL/6 mice was collected and diluted with PBS in a 1:2 ratio. The blood was frozen and thawed three times and then centrifuged at 21,600 g for 1.5 hours at 4° C. The supernatant was collected and filtered (0.22 μM Nalgene filter, Rochester, N.Y.). The solution was dialyzed against 0.9% saline overnight at 4° C. Then the solution was concentrated using 3,000 MWCO Centricon Centrifugal filter Devices (Fisher Scientific, Pittsburgh, Pa.). The final concentration of the tetrameric hemoglobin solution was 4 g/dl.

Measurements of Hemoglobin and Methemoglobin Concentration

Hemoglobin and methemoglobin concentration in whole blood and plasma were determined by the cyanomethemoglobin method measuring OD at 540 nm and 630 nm with a Spectrophotometer-Biomate 3 (Thermoelectron Corporation, Waltham, Mass.).

Intravenous Injection (Tail Vein) of Tetrameric Hemoglobin Solution

The mouse was placed in a restrainer for this procedure. All mice were handled briefly and gently to inject a tetrameric hemoglobin solution into a lateral tail vein. Before injection, the tail was warmed under an infra-red heat lamp for 5 minutes to enable access to the vein. The injection volume was 0.012 ml/g body weight for each mouse. Infusion was done during the course of one minute.

Nitric Oxide Delivery

With the use of volumetrically calibrated flowmeters (Cole-Parmer, Vernon Hills, Ill.), nitric oxide gas (800 ppm in nitrogen; INO Therapeutics, Clinton, N.J.) was given to awake mice through a face mask at a final concentration of 80 ppm (INO Therapeutics, Clinton, N.J.). The nitric oxide, nitrogen dioxide and oxygen (21%) levels were continuously monitored (INOvent delivery system, Datex-Ohmeda, Madison, Wis.).

Hemodynamic Effects of Nitric Oxide Inhalation

The effects of breathing nitric oxide on systolic tail blood pressure after the infusion of murine tetrameric hemoglobin solution were monitored every 10 minutes for the 1$^{st}$ hour and every 20 minutes for the rest of the experiments. Blood hemoglobin and methemoglobin levels were measured every 15 minutes in the nitric oxide pretreatment group, wherein all mice breathed nitric oxide at 80 ppm for 1 hour before infusion. Hemoglobin and methemoglobin levels in whole blood and plasma were measured in additional mice after the intravenous infusion of tetrameric hemoglobin solution at 10 minutes and 60 minutes while breathing nitric oxide at 8 ppm or 80 ppm throughout the experiment.

Measurements of Tail-Cuff Blood Pressure in Awake Mice

Systolic blood pressure was measured with a non-invasive tail-cuff machine (XBP 1000, Kent Scientific, Torrington, Conn.) in wild type mice and NOS3$^{-/-}$ mice. Mice were first subjected to one or two practice sessions to acclimate them to the device. The mouse was placed in a restrainer for a short period of time (<1 minute to start), then kept in the restrainer for longer times to acclimate to the device. The degree of acclimatization was judged by the absence of agitation in the device. After a few days of practice sessions, mice were restrained in a commercial mouse restraint device (Kent Scientific, Torrington, Conn.).

Tail systolic blood pressures were measured as follows: (1) baseline blood pressure before infusion (saline or murine whole blood infusions provided to control groups and tetrameric hemoglobin was given to the treated group); (2) blood pressure after infusion of saline or tetrameric hemoglobin solution; (3) blood pressure after infusion of tetrameric hemoglobin solution while breathing air or air containing nitric oxide; and (4) blood pressure before and after pretreatment with 80 ppm nitric oxide for 15 minutes or 1 hour.

Statistical Analysis

All values are expressed as mean±SEM. Data were analyzed using ANOVA. The difference in hemodynamic parameters before and after infusion of murine tetrameric hemoglobin or nitric oxide inhalation was examined by a paired t-test for repeated measurements. P values less than 0.05 were considered significant (as indicated by a * in the figures).

Results

Tail systolic blood pressure was measured in awake wild type mice and NOS3−/− mice before and after intravenous injection of 0.012 ml/g body weight of murine tetrameric hemoglobin solution. Measurements were taken 10 minutes before and 10 minutes after injection of the hemoglobin solution. Tetrameric hemoglobin injection resulted in a significant increase in systolic blood pressure in wild type mice but not in NOS3−/− mice (FIG. 1).

Figure 2:
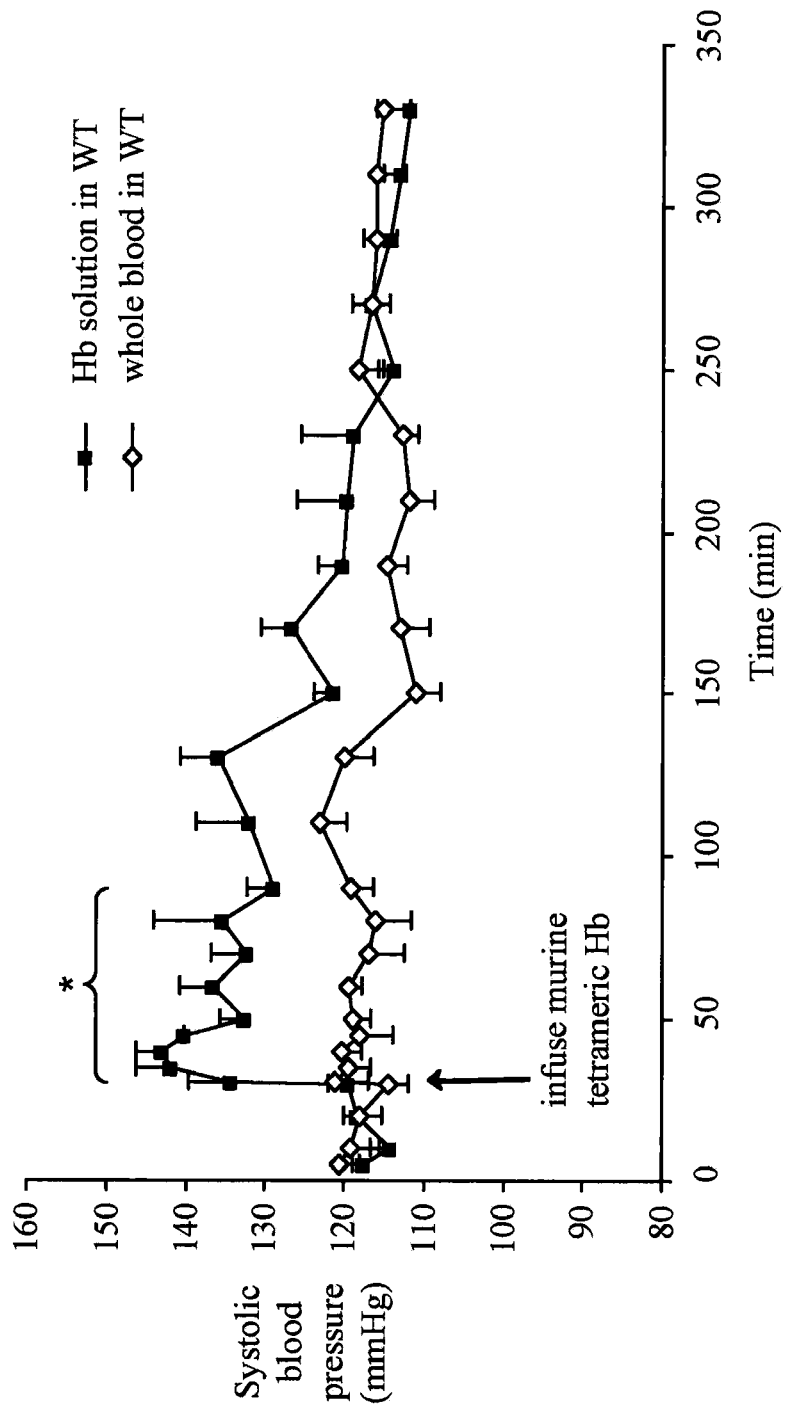
FIG. 2 is a graph depicting tail systolic blood pressure in awake wild type mice before and after intravenous injection of whole blood or murine tetrameric hemoglobin solution.

Tail systolic arterial blood pressure was measured in wild type mice before and after intravenous injection of whole blood or murine tetrameric hemoglobin solution. For the "whole blood" group, 0.012 ml/g body weight of whole murine blood was administered by intravenous injection (n=7). For the "Hb solution" group, 0.012 ml/g body weight of murine tetrameric hemoglobin solution (at a concentration of 620 mM) was administered by intravenous injection (n=4). Infusion of the murine tetrameric hemoglobin solution triggered a significant elevation in blood pressure, whereas injection of whole murine blood did not (FIG. 2).

Example 2

Figure 3:
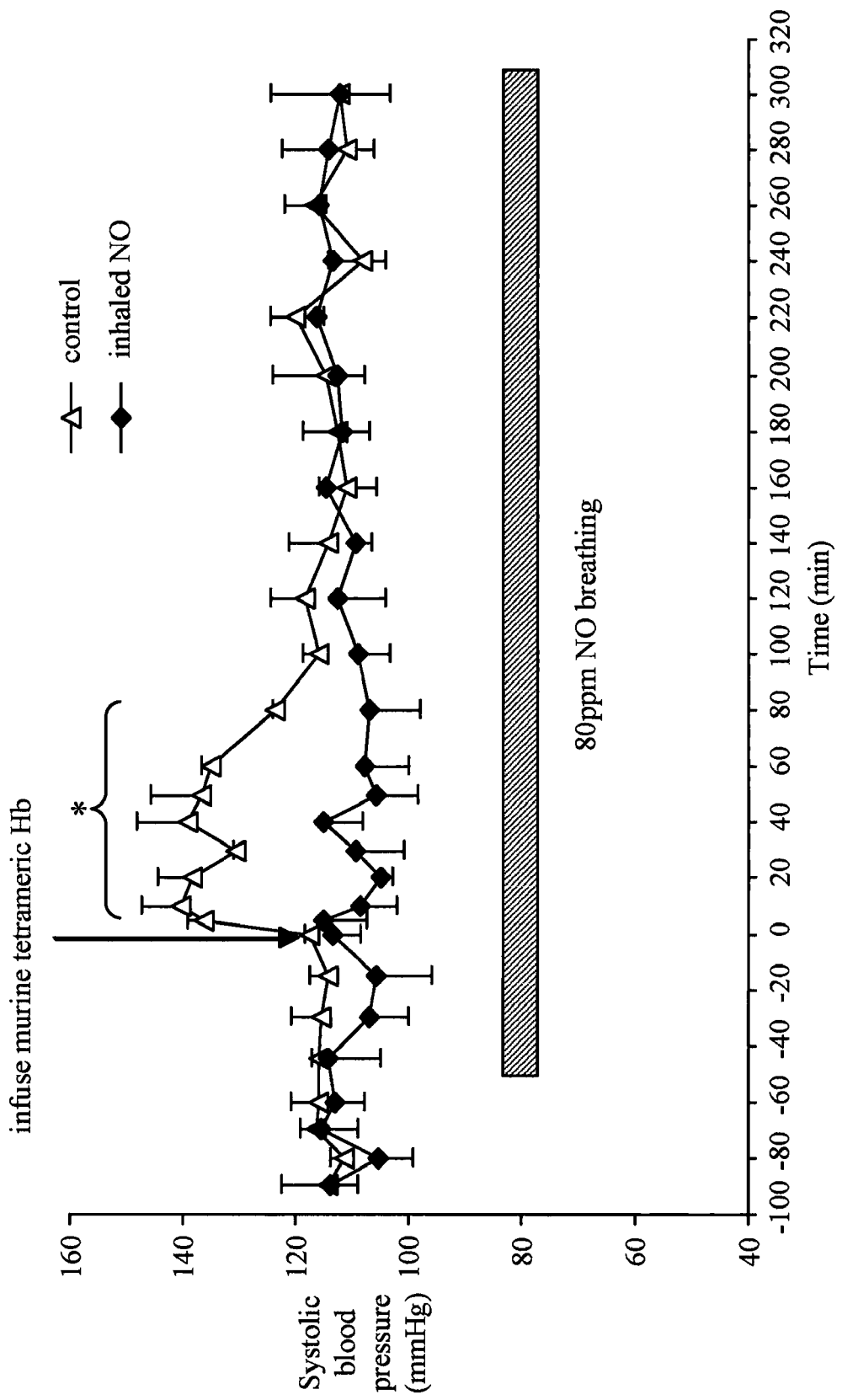
FIG. 3 is a graph depicting tail systolic blood pressure in awake wild type mice breathing 80 ppm nitric oxide continuously before and subsequent to intravenous injection of murine tetrameric hemoglobin solution.

Continuous Nitric Oxide Inhalation Before and Subsequent to Infusion of a Tetrameric Hemoglobin Solution Prevents Increase in Systolic Blood Pressure and Converts Plasma Hemoglobin to Methemoglobin Tail systolic blood pressure was measured in awake wild type mice (n=4) after intravenous injection of 0.012 ml/g body weight of murine tetrameric hemoglobin solution. The "inhaled NO" group inhaled 80 ppm nitric oxide in air and the "control" group inhaled air. Breathing 80 ppm nitric oxide continuously before and subsequent to infusion of the murine tetrameric hemoglobin solution prevented a hemoglobin-induced elevation in systolic blood pressure (FIG. 3).

Figure 4:
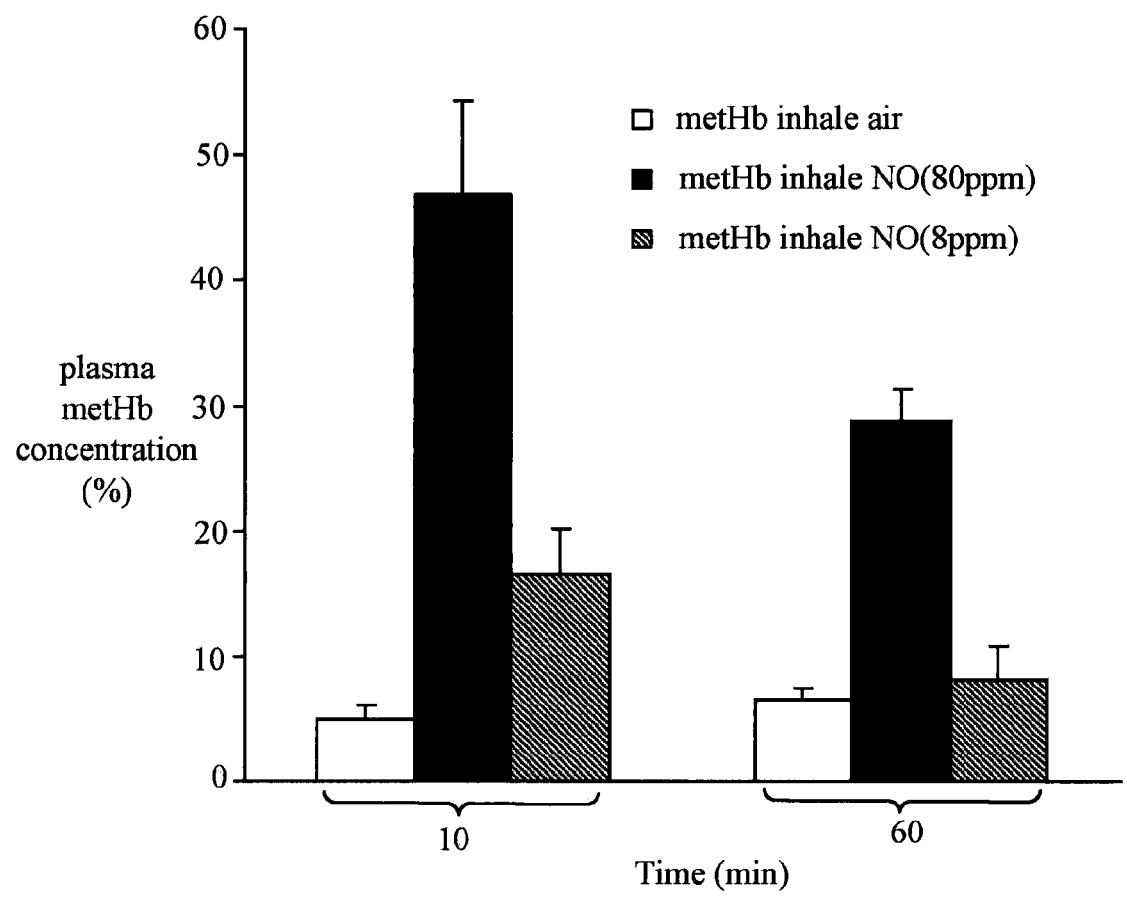
FIG. 4 is a graph depicting plasma methemoglobin concentration in awake wild type mice breathing air, 80 ppm nitric oxide in air, or 8 ppm nitric oxide in air continuously before and subsequent to intravenous injection of murine tetrameric hemoglobin solution.

Methemoglobin concentration in plasma was measured after intravenous injection of 0.012 ml/g body weight of murine tetrameric hemoglobin solution to wild type mice while breathing either air (n=4), 80 ppm nitric oxide in air (n=4), or 8 ppm nitric oxide in air (n=7). Administration of the murine tetrameric hemoglobin solution while breathing 80 ppm nitric oxide resulted in a conversion of a significant proportion of plasma hemoglobin to inactive methemoglobin (FIG. 4). Measurements were taken 10 minutes and 60 minutes after injection.

Example 3

Figure 5:
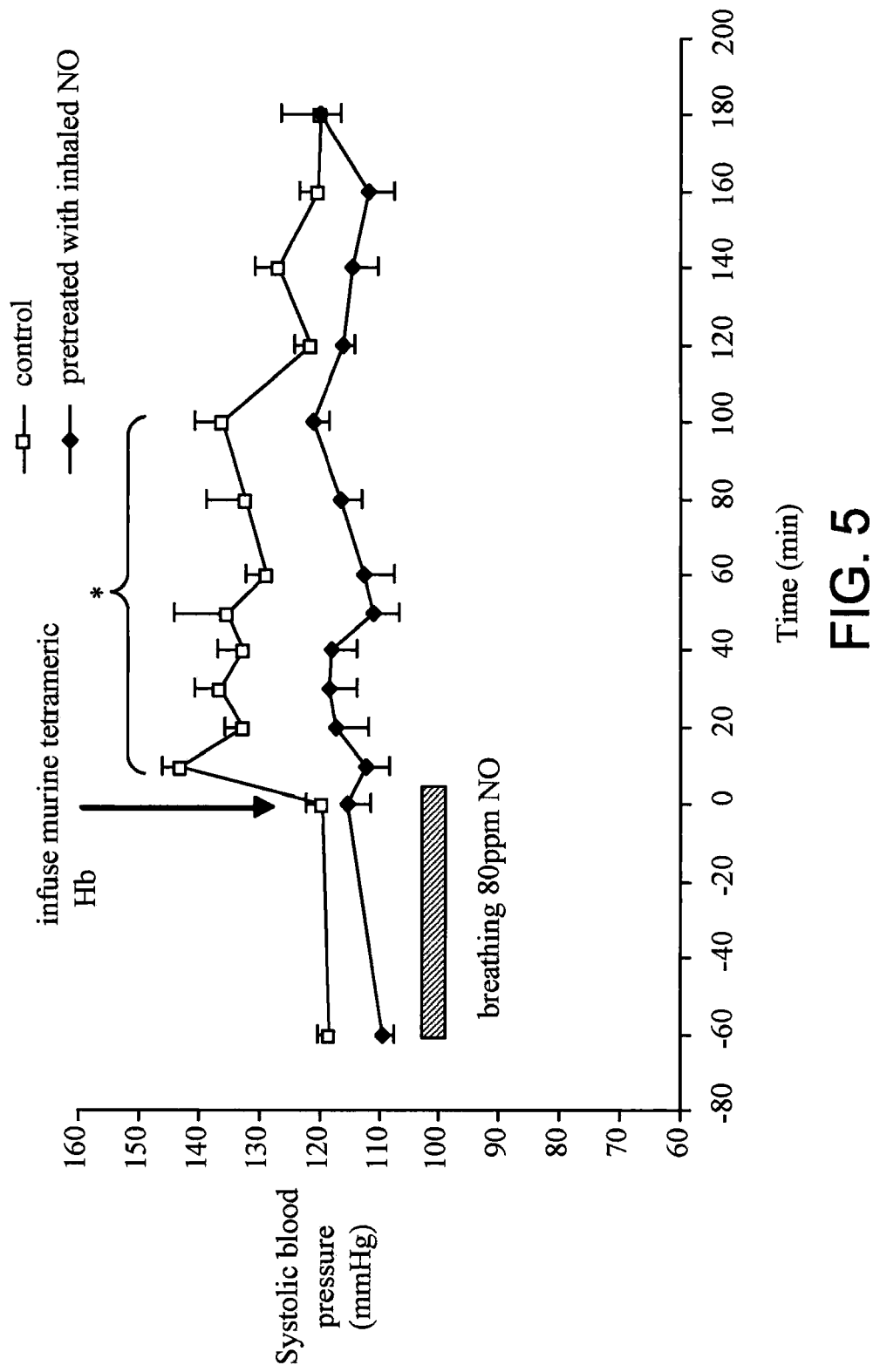
FIG. 5 is a graph depicting tail systolic blood pressure in awake wild type mice breathing 80 ppm nitric oxide in air continuously for one hour before intravenous injection of murine tetrameric hemoglobin solution.

Continuous Nitric Oxide Inhalation Before Infusion of a Tetrameric Hemoglobin Solution Prevents Increase in Systolic Blood Pressure and does not Convert Plasma Hemoglobin to Methemoglobin Tail systolic blood pressure was measured in wild type mice before and after intravenous injection of 0.012 ml/g body weight of murine tetrameric hemoglobin solution. "Control" mice received the murine tetrameric hemoglobin solution but did not breathe nitric oxide. "Pretreated with inhaled NO" mice inhaled 80 ppm nitric oxide in air for one hour before receiving the intravenous murine tetrameric hemoglobin solution (n=7). Breathing 80 ppm nitric oxide continuously for one hour before infusion of the murine tetrameric hemoglobin solution (and terminating nitric oxide inhalation at the time of infusion) prevented a hemoglobin-induced elevation in systolic blood pressure (FIG. 5).

Figure 6:
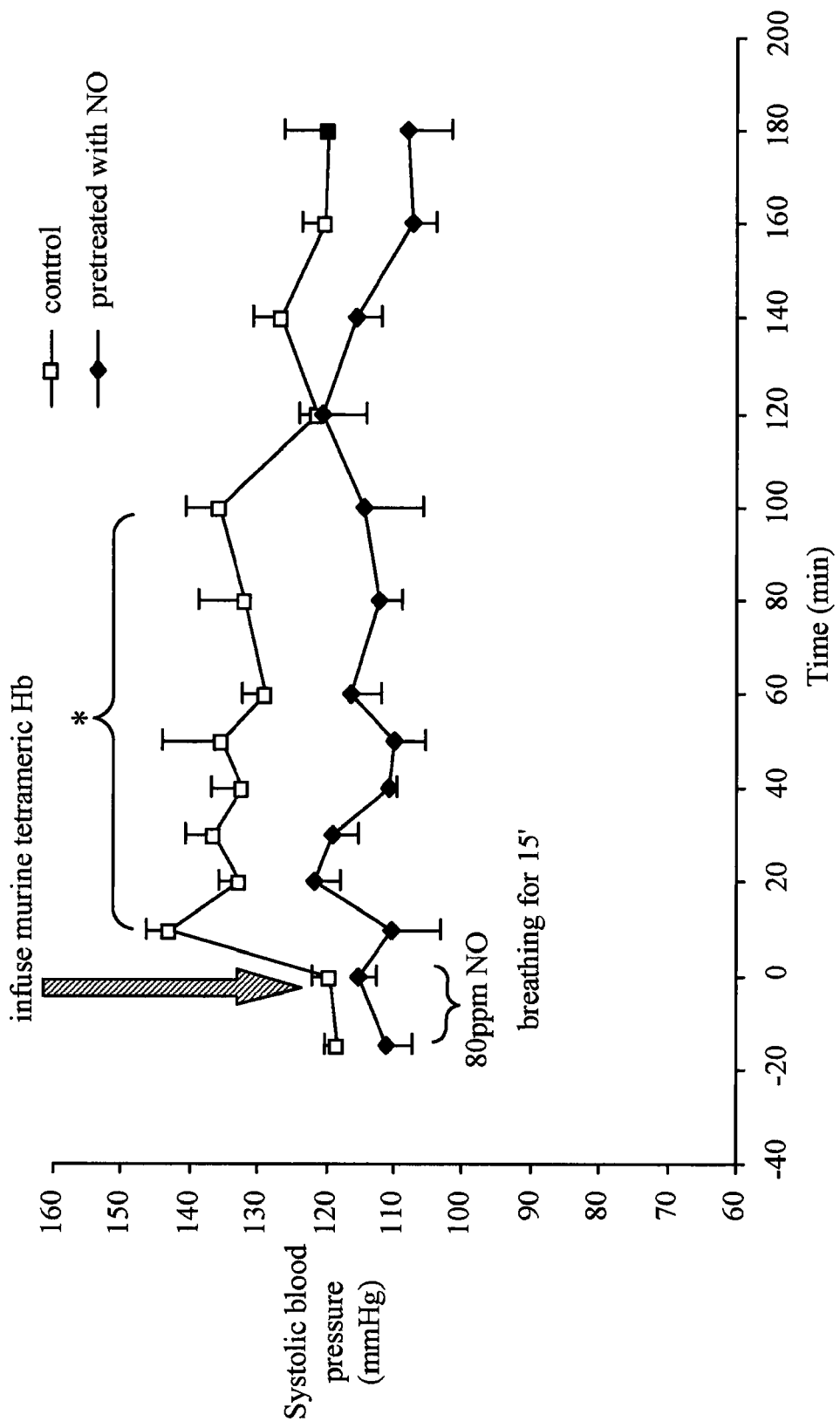
FIG. 6 is a graph depicting tail systolic blood pressure in awake wild type mice breathing 80 ppm nitric oxide in air continuously for 15 minutes before intravenous injection of murine tetrameric hemoglobin solution.

Tail systolic blood pressure was measured in wild type mice before and after intravenous injection of 0.012 ml/g body weight of murine tetrameric hemoglobin solution. "Control" mice received the murine tetrameric hemoglobin solution but did not breathe nitric oxide. "Pretreated with NO" mice inhaled 80 ppm nitric oxide in air for 15 minutes before receiving the intravenous murine tetrameric hemoglobin solution (n=4). Breathing 80 ppm nitric oxide continuously for 15 minutes before infusion of the murine tetrameric hemoglobin solution (and terminating nitric oxide inhalation at the time of infusion) prevented a hemoglobin-induced elevation in systolic blood pressure (FIG. 6).

Figure 7:
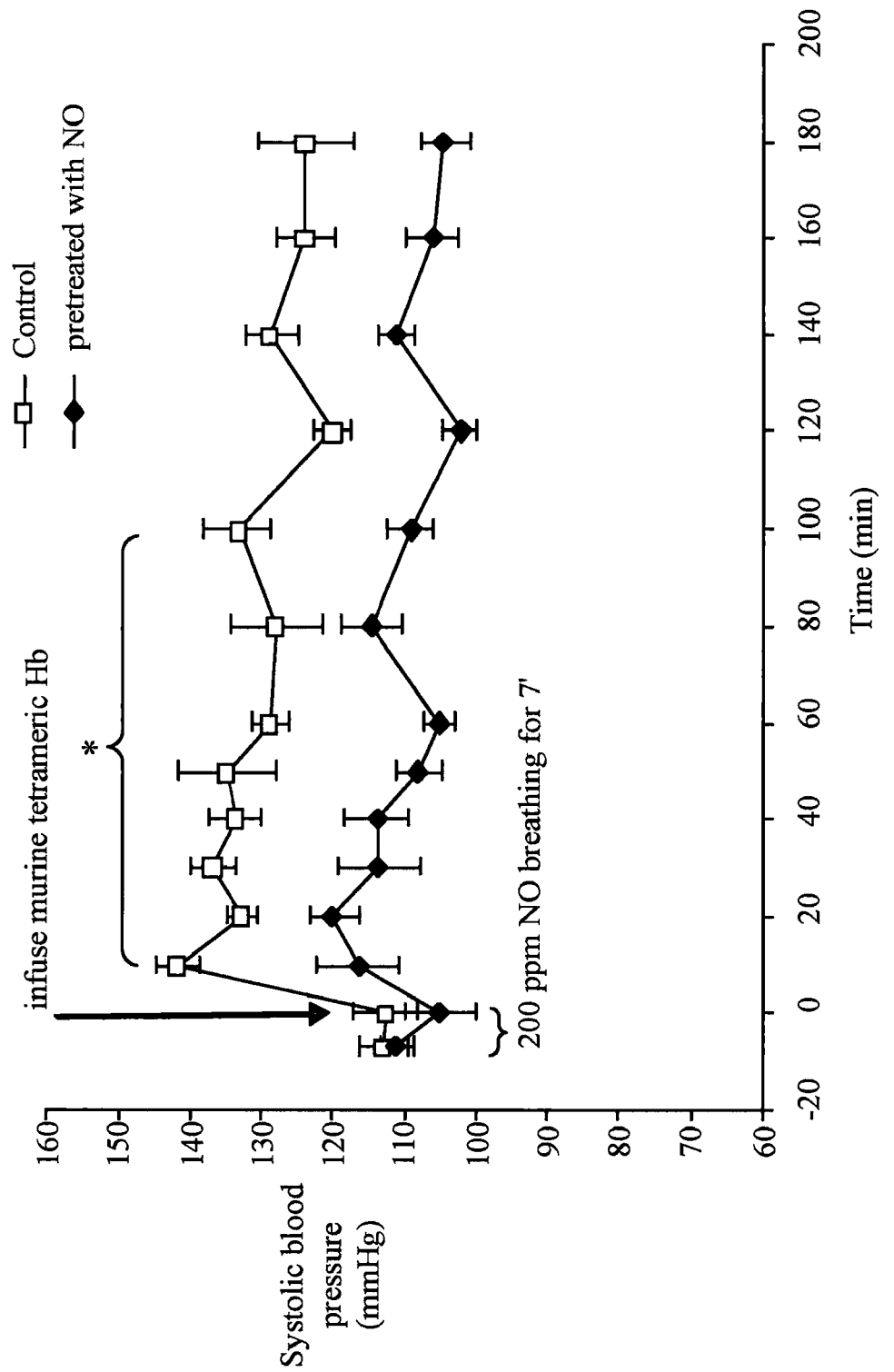
FIG. 7 is a graph depicting tail systolic blood pressure in awake wild type mice breathing 200 ppm nitric oxide in air continuously for 7 minutes before intravenous injection of murine tetrameric hemoglobin solution.

Tail systolic blood pressure was measured in wild type mice before and after intravenous injection of 0.012 ml/g body weight of murine tetrameric hemoglobin solution. "Control" mice received the murine tetrameric hemoglobin solution but did not breathe nitric oxide (n=6). "Pretreated with NO" mice inhaled 200 ppm nitric oxide in air for 7 minutes before receiving the intravenous murine tetrameric hemoglobin solution (n=8). Breathing 200 ppm nitric oxide continuously for 7 minutes before infusion of the murine tetrameric hemoglobin solution (and terminating nitric oxide inhalation at the time of infusion) prevented a hemoglobin-induced elevation in systolic blood pressure (FIG. 7).

Figure 8:
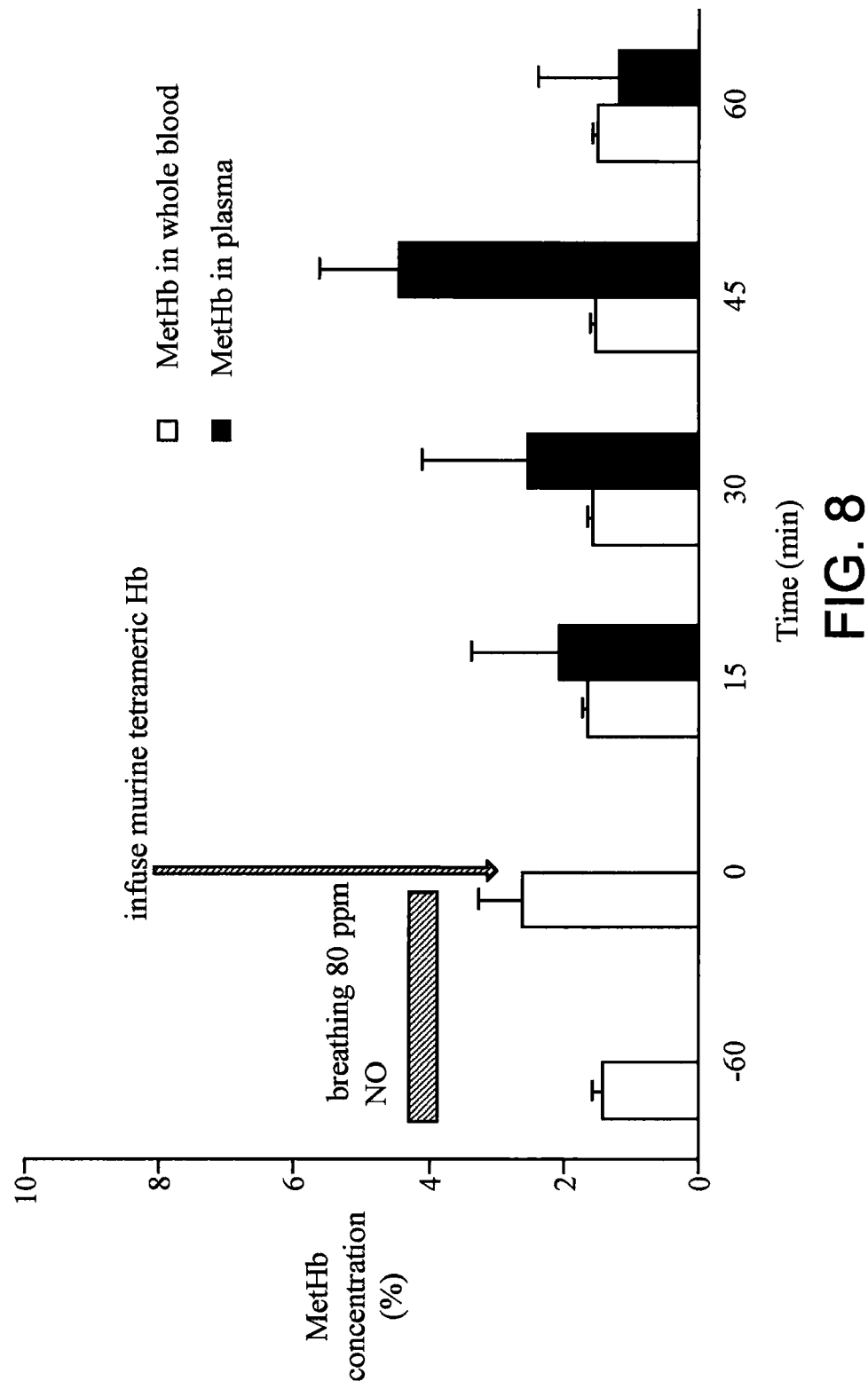
FIG. 8 is a graph depicting whole blood and plasma methemoglobin concentration in awake wild type mice breathing 80 ppm nitric oxide in air before intravenous injection of murine tetrameric hemoglobin solution.

Methemoglobin concentration in whole blood and plasma was measured in wild type mice before and after breathing 80 ppm nitric oxide for 1 hour (and before and after infusion of murine tetrameric hemoglobin solution). Samples were taken (i) before both nitric oxide breathing and hemoglobin administration, (ii) after nitric oxide breathing but before hemoglobin administration, and (iii) after both nitric oxide breathing and intravenous injection of murine tetrameric hemoglobin solution (samples taken at 15 minute intervals). Breathing 80 ppm nitric oxide continuously for one hour before infusion of the murine tetrameric hemoglobin solution (and terminating nitric oxide inhalation at the time of infusion) resulted in conversion of less than approximately 5% of plasma hemoglobin to methemoglobin (FIG. 8).

Example 4

Invasive Hemodynamic Measurements in Anesthetized Mice

To explore the mechanisms by which infusion of tetrameric hemoglobin causes systemic hypertension in awake wild type mice, invasive hemodynamic measurements were performed in anesthetized wild type and NOS3$^{-/-}$ mice before and three minutes after infusion of murine tetrameric hemoglobin or whole murine blood as a control. Mice were anesthetized with an intraperitoneal injection of ketamine (100 mg/kg) and xylazine (5 mg/kg). Muscle relaxation was obtained by adding pancuronium (5 μg/g) after tracheal intubation. Volume-controlled ventilation was provided at a respiratory rate of 120 breaths/minute, tidal volume of 10 μl/g, with an inspired $O_2$ fraction of 1.0 (Mini Vent 845, Harvard Apparatus, Holliston, Mass.). Two saline-filled PE-10 catheters were inserted separately via the jugular veins; one for monitoring central venous pressure (CVP) and the other for infusion of whole blood or tetrameric hemoglobin solution. A Millar pressure-volume catheter was inserted retrograde via the right carotid artery into the left ventricle (1.4F, model SPR839, Millar Instruments Inc., Houston, Tex.). After obtaining stable hemodynamic measurements, whole blood (1.44 g Hb/kg) or murine tetrameric Hb solution (0.48 g/kg) was infused through the jugular vein, at a rate of 100 μl/min for 3 min. PVAN software was used to analyze left ventricular pressure-volume loop data (Conductance Technologies Inc., San Antonio, Tex.).

At baseline, left ventricular (LV) end-diastolic pressure (LVEDP), maximum rate of developed LV pressure ($dP/dt_{max}$), minimum rate of developed LV pressure ($dP/dt_{min}$), cardiac output (CO), arterial elastance (Ea), time constant of isovolumic relaxation ($\tau$), and central venous pressure (CVP) were similar between genotypes (Table 1). LV end-systolic pressure (LVESP), Ea, and systemic vascular resistance (SVR) were greater at baseline in NOS3$^{-/-}$ than in wild type mice ($p<0.05$ for all three). Infusion of murine whole blood did not change the heart rate (HR), LVESP, LVEDP, CO, SVR, Ea, $\tau$, or CVP in either genotype. However, intravenous infusion of murine tetrameric hemoglobin in wild type mice increased LVESP, LVEDP, SVR, Ea, and $\tau$ and decreased CO without affecting $dP/dt_{max}$, $dP/dt_{min}$, or CVP. In contrast, the infusion of murine tetrameric hemoglobin into NOS3$^{-/-}$ mice did not alter HR, LVESP, LVEDP, CO, $dP/dt_{max}$, $dP/dt_{min}$, SVR, Ea, $\tau$, or CVP. These results demonstrate that infusion of tetrameric hemoglobin causes systemic vasoconstriction and impairs cardiac diastolic function via a mechanism that depends on NOS3. Furthermore, pretreatment of wild type mice with inhaled nitric oxide at 80 ppm for 15 minutes abolished the increase of LVESP, LVEDP, SVR, Ea, and $\tau$ induced by murine tetrameric hemoglobin infusion (Table 1).

TABLE 1

Comparison of Cardiac Function and Systemic Hemodynamic Measurements in Wild Type and NOS3 Knockout Mice

| | WT | | | | NOS3$^{-/-}$ | |
|---|---|---|---|---|---|---|
| | Baseline | Whole Blood | Baseline | Tetrameric Hb | Baseline | Whole Blood |
| HR (bpm) | 623 ± 14 | 623 ± 15 | 608 ± 13 | 602 ± 12 | 561 ± 14 | 564 ± 12 |
| LVESP (mmHg) | 101 ± 3 | 100 ± 4 | 101 ± 3 | 158 ± 5* | 120 ± 5† | 116 ± 4 |
| LVEDP (mmHg) | 6 ± 1 | 6 ± 1 | 6 ± 1 | 12 ± 1* | 6 ± 1 | 7 ± 2 |
| $dP/dt_{max}$ (mmHg/s) | 13800 ± 1200 | 13480 ± 1340 | 12060 ± 1170 | 12260 ± 750 | 13400 ± 1100 | 12040 ± 860 |
| $dP/dt_{min}$ (mmHg/s) | −12100 ± 630 | −12800 ± 980 | −11730 ± 540 | −10110 ± 640 | −14150 ± 800 | −14070 ± 670 |
| CO (ml/min) | 12 ± 1 | 12 ± 1 | 12 ± 1 | 10 ± 1* | 9 ± 1 | 10 ± 1 |
| SVR (dynes*sec/cm$^2$) | 7 ± 0 | 7 ± 0 | 9 ± 1 | 16 ± 1* | 15 ± 5† | 16 ± 4 |
| Ea (mmHg/μl) | 5 ± 0 | 5 ± 0 | 5 ± 0 | 9 ± 1* | 8 ± 1† | 8 ± 1 |
| Tau (msec) | 5 ± 0 | 5 ± 0 | 5 ± 0 | 8 ± 1* | 6 ± 1 | 6 ± 1 |
| CVP (mmHg) | 3 ± 0 | 3 ± 0 | 3 ± 0 | 3 ± 0 | 3 ± 0 | 4 ± 0 |

TABLE 1-continued

Comparison of Cardiac Function and Systemic Hemodynamic Measurements in Wild Type and NOS3 Knockout Mice

| | NOS3$^{-/-}$ | | WT ± iNO | |
|---|---|---|---|---|
| | Baseline | Tetrameric Hb | Baseline | Tetrameric Hb |
| HR (bpm) | 545 ± 14 | 553 ± 18 | 607 ± 19 | 603 ± 20 |
| LVESP (mmHg) | 118 ± 4 | 117 ± 5 | 100 ± 2 | 101 ± 4 |
| LVEDP (mmHg) | 6 ± 1 | 8 ± 2 | 5 ± 1 | 6 ± 1 |
| dP/dt$_{max}$ (mmHg/s) | 12340 ± 840 | 13736 ± 606 | 12420 ± 970 | 11230 ± 750 |
| dP/dt$_{min}$ (mmHg/s) | −12900 ± 850 | −12290 ± 620 | −11610 ± 700 | −10650 ± 430 |
| CO (ml/min) | 9 ± 1 | 9 ± 1 | 12 ± 1 | 12 ± 1 |
| SVR (dynes*sec/cm$^2$) | 15 ± 2 | 15 ± 2 | 8 ± 1 | 8 ± 1‡ |
| Ea (mmHg/μl) | 8 ± 1 | 8 ± 1 | 5 ± 1 | 5 ± 0 |
| Tau (msec) | 6 ± 0 | 6 ± 1 | 5 ± 1 | 5 ± 0 |
| CVP (mmHg) | 3 ± 0 | 4 ± 0 | 3 ± 0 | 4 ± 0 |

WT (wild type): infusion of whole blood or murine tetrameric Hb while breathing air in WT mice (n = 15);
NOS3$^{-/-}$: infusion of whole blood or murine tetrameric Hb while breathing air in NOS3 knockout mice (n = 13);
WT + iNO: breathing 80 ppm NO in air for 15 min, followed by discontinuation of NO gas breathing and infusion of murine tetrameric Hb solution in WT mice (n = 12);
HR: heart rate;
LVESP: left ventricular end-systolic pressure;
LVEDP: left ventricular end-diastolic pressure;
dP/dt$_{max}$: maximum rate of developed left ventricular pressure;
dP/dt$_{min}$: minimum rate of developed left ventricular pressure;
CO: cardiac output;
SVR: systemic vascular resistance;
Ea: arterial elastance;
Tau: time constant of isovolumic relaxation;
CVP: central venous pressure (n = 5).
Values are mean ± SEM.
*p < 0.05 value differs versus baseline.
†p < 0.05 value differs versus WT baseline.
‡p < 0.05 value differs versus infusion of tetrameric Hb in WT mice.

Example 5

Effect of Intravenous Sodium Nitrite Pretreatment on the Hypertensive Response to Subsequent Infusion of a Tetrameric Hemoglobin Solution Sodium nitrite (Sigma-Aldrich, St. Louis, Mo.) was dissolved in phosphate buffered saline (PBS), and the pH was adjusted to 7.4. A final volume of 50 μl PBS solution containing 48 nmol (approximately 0.13 mg/kg) sodium nitrite was administered via a tail vein and was followed five minutes later by an intravenous infusion of murine tetrameric hemoglobin solution (0.48 g/kg). The dose of sodium nitrite was chosen to approximate the plasma nitrite levels measured in mice breathing 80 ppm nitric oxide for one hour (1-2 μM at peak levels). Tail-cuff systolic blood pressure (SBP, mmHg) was measured in awake mice before and after the infusion of whole blood (n=7), murine tetrameric hemoglobin (n=5), or sodium nitrite followed by a murine tetrameric hemoglobin infusion (n=5).

Figure 10A:
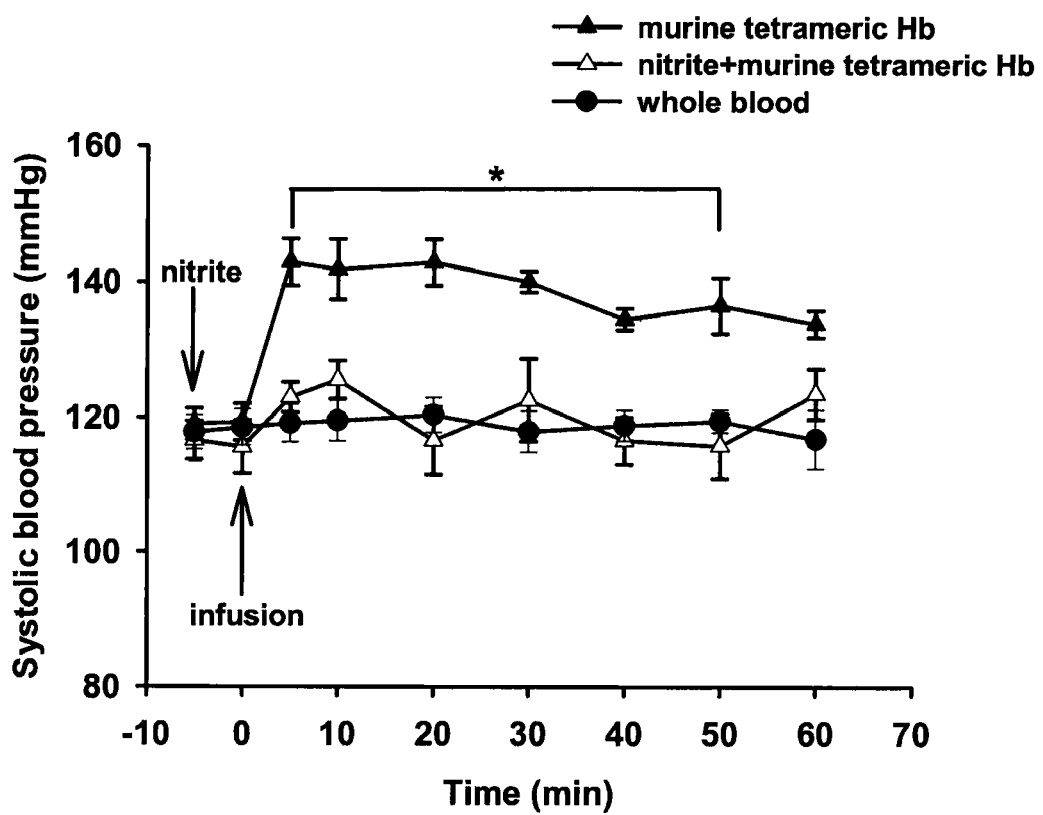
FIG. 10A is a graph depicting tail systolic blood pressure in awake wild type mice that received an intravenous infusion of sodium nitrite before intravenous injection of murine tetrameric hemoglobin solution.
Figure 10B:
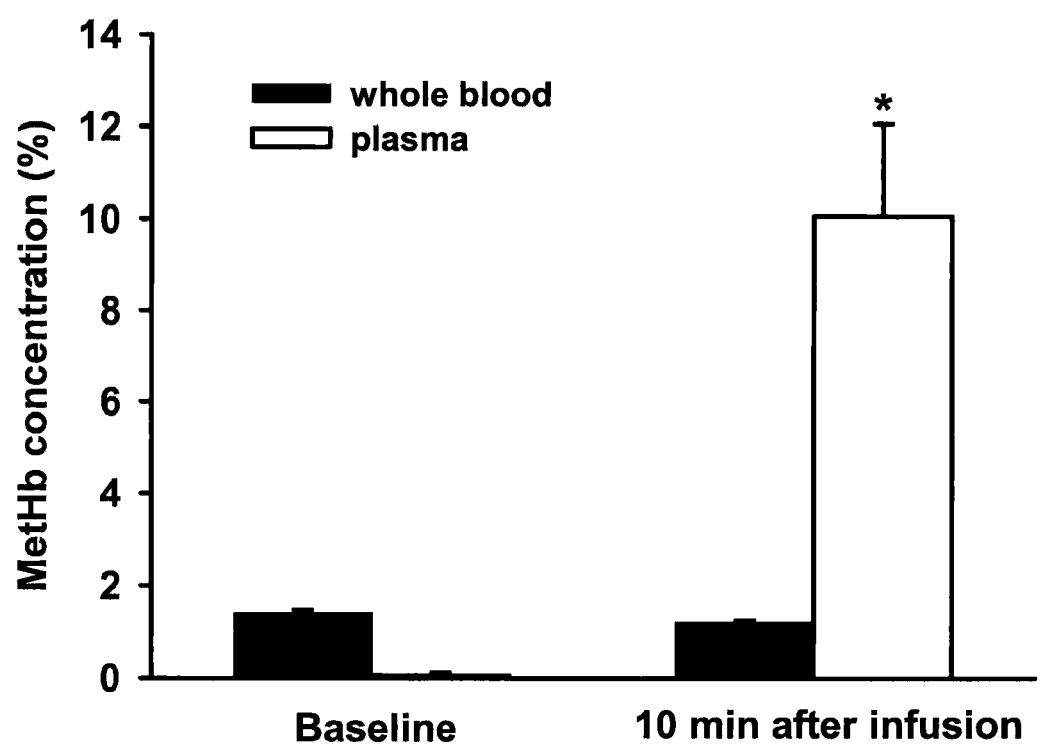
FIG. 10B is a graph depicting methemoglobin concentration in awake wild type mice that received an intravenous infusion of sodium nitrite before intravenous injection of murine tetrameric hemoglobin solution.

Nitrite administration did not alter blood pressure before murine tetrameric hemoglobin was infused. Administration of nitrite blocked the systemic hypertension caused by the subsequent infusion of murine tetrameric hemoglobin (FIG. 10A; *p<0.05 differs versus both the whole blood group and the nitrite plus murine tetrameric hemoglobin group). However, 10 minutes after murine tetrameric hemoglobin infusion, the plasma methemoglobin level increased to 10±2% (FIG. 10B; *p<0.05 differs versus baseline plasma level). This concentration of methemoglobin (10±2%) is insufficient to account for the ability of nitrite to block tetrameric hemoglobin-induced hypertension because infusion of murine tetrameric hemoglobin solution containing 14.5% methemoglobin caused systemic hypertension.

Example 6

Continuous Nitric Oxide Inhalation Before Infusion of HBOC-201 Prevents Induction of Systemic Vasoconstriction but not Pulmonary Vasoconstriction in Lambs Lambs were briefly anesthetized, given a tracheostomy, the internal jugular vein was percutaneously catheterized and a flow directed Swan Ganz catheter passed into the pulmonary artery to permit measurements of central hemodynamics and cardiac output by thermaldilution. An arterial line was placed in the carotid artery. Animals were allowed several hours to awaken from anesthesia and were studied awake and restrained in a harness. Three groups of lambs were studied: (1) "autologous whole blood" animals donated autologous blood, which was stored with heparin anti-coagulation at 4° C.—two days later they received an infusion of their 37° C. autologous whole blood (12 ml/kg over 20 minutes) while breathing at $FiO_2$=0.3 (n=3); (2) "HBOC-201" animals received an infusion of HBOC-201 (12 ml/kg over 20 minutes) while breathing at $FiO_2$=0.3 (n=3); and (3) "HBOC-201 after iNO" animals inhaled 80 ppm nitric oxide at $FiO_2$=0.3 for one hour before receiving an infusion of HBOC-201 (12 ml/kg over 20 minutes) (n=5). Systemic vascular resistance (SVR) and pulmonary vascular resistance (PVR) were calculated using standard formulae as follows: [SVR (dynes*sec/$cm^2$)=(MAP−CVP)/CO*79.96]; and [PVR (dynes*sec/$cm^2$)=(PAP−PCWP)/CI*79.96].

Figure 11:
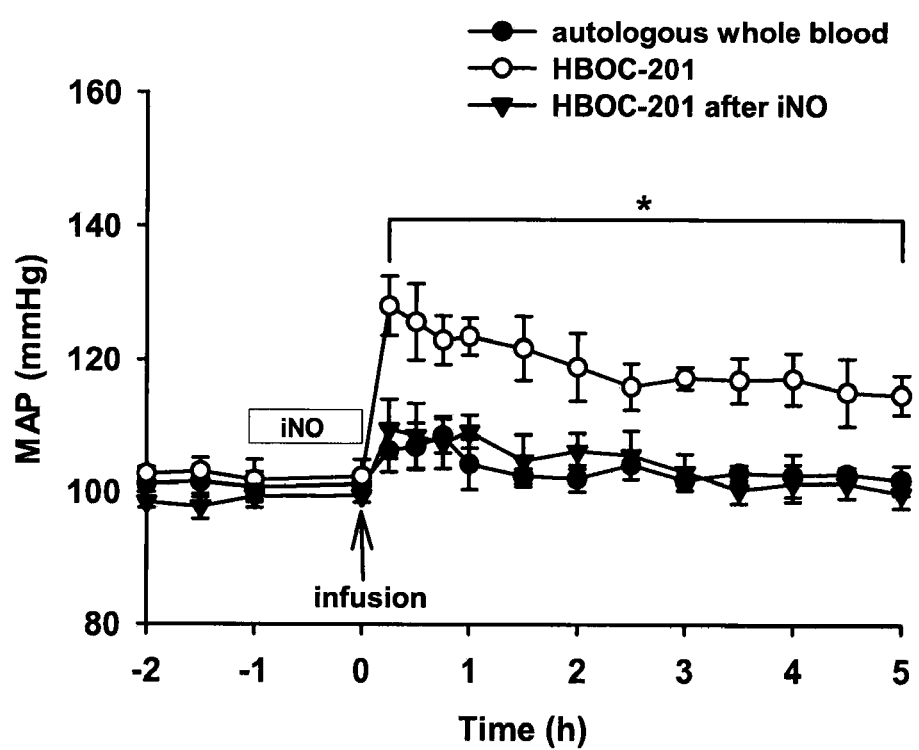
FIG. 11 is a graph depicting mean systemic arterial pressure (MAP) in awake lambs breathing air or 80 ppm nitric oxide in air continuously for one hour before infusion of HBOC-201 or given an infusion of 37 degrees C. autologous blood stored in heparin for 2 days.
Figure 12:
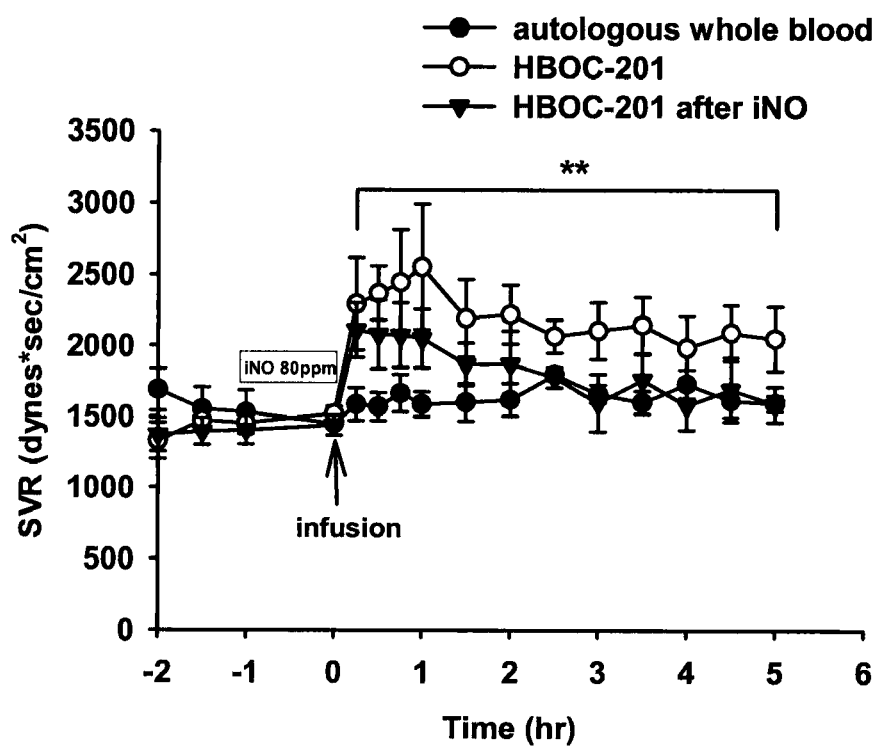
FIG. 12 is a graph depicting systemic vascular resistance (SVR) in awake lambs breathing air or 80 ppm nitric oxide in air continuously for one hour before infusion of HBOC-201 or given an infusion of autologous blood.

Mean arterial pressure and systemic vascular resistance were measured before and after infusion of autologous whole blood or HBOC-201. Breathing 80 ppm nitric oxide continuously for one hour before infusion of HBOC-201 (and terminating nitric oxide inhalation immediately before the time of infusion) blocked the increase in mean arterial pressure (FIG. 11; *$p<0.05$ HBOC-201 alone differs from autologous whole blood) and systemic vascular resistance (FIG. 12) that otherwise occurred after HBOC-201 infusion.

Figure 13:
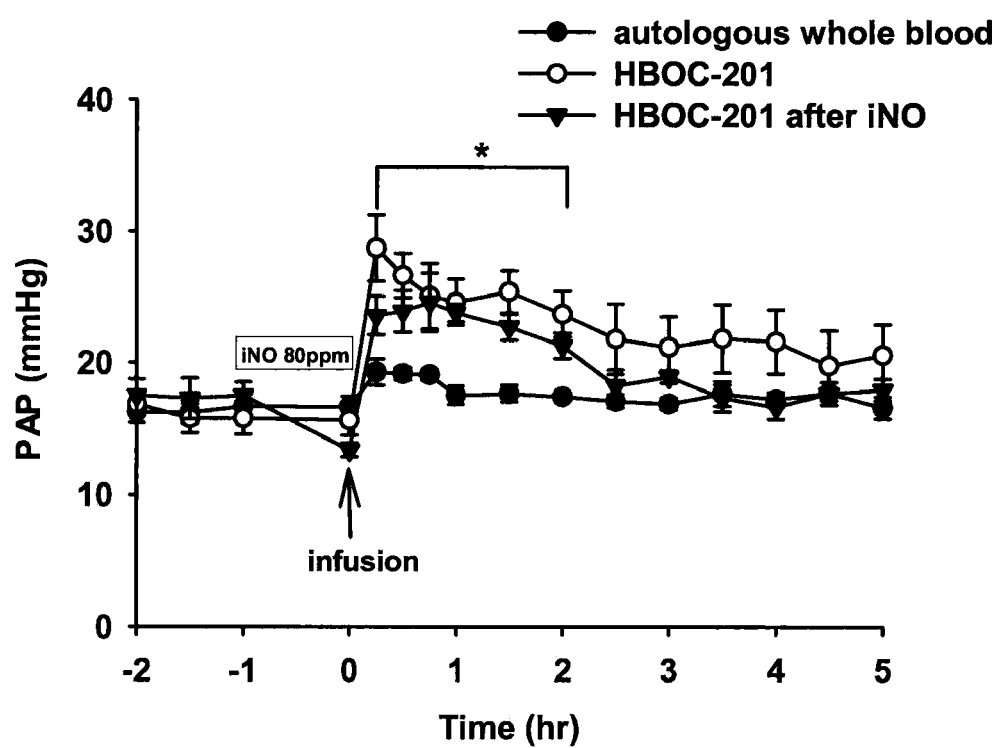
FIG. 13 is a graph depicting mean pulmonary arterial pressure (PAP) in awake lambs breathing air or 80 ppm nitric oxide in air continuously for one hour before infusion of HBOC-201 or given an infusion of autologous blood.
Figure 14:
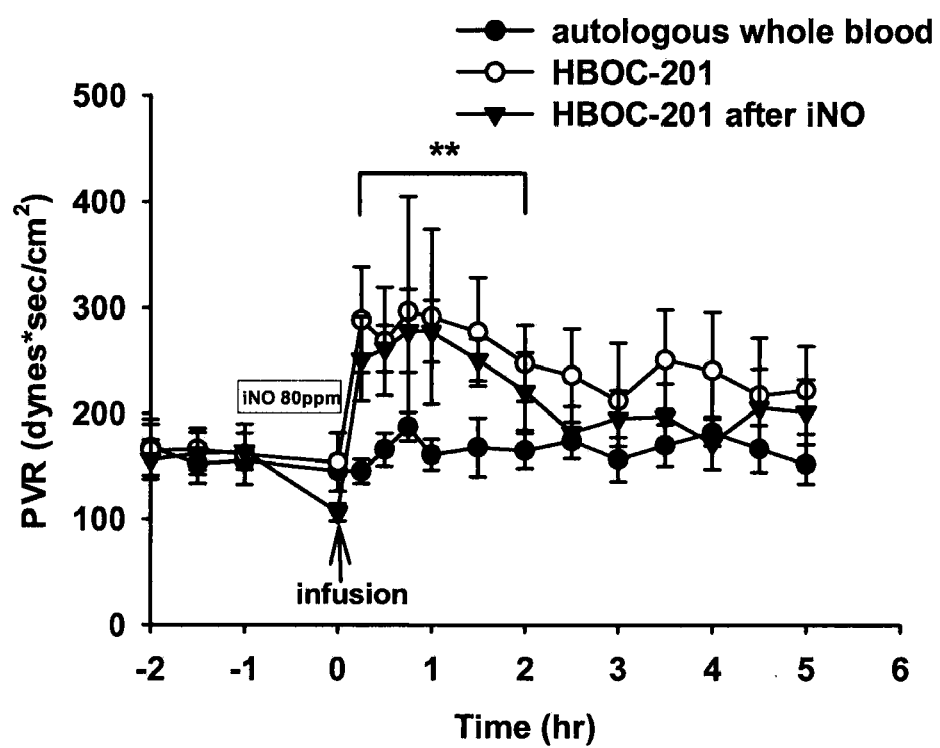
FIG. 14 is a graph depicting pulmonary vascular resistance (PVR) in awake lambs breathing air or 80 ppm nitric oxide in air continuously for one hour before infusion of HBOC-201 or given an infusion of autologous blood.

Pulmonary arterial pressure and pulmonary vascular resistance were measured before and after infusion of autologous whole blood or HBOC-201. Breathing 80 ppm nitric oxide continuously for one hour before infusion of HBOC-201 (and terminating nitric oxide inhalation immediately before the time of infusion) did not block the increase in pulmonary arterial pressure (FIG. 13; *$p<0.05$ HBOC-201 differs from autologous blood) and pulmonary vascular resistance (FIG. 14; **$p<0.05$ HBOC-201 alone differs from autologous whole blood) that occurred after HBOC-201 infusion.

Figure 15:
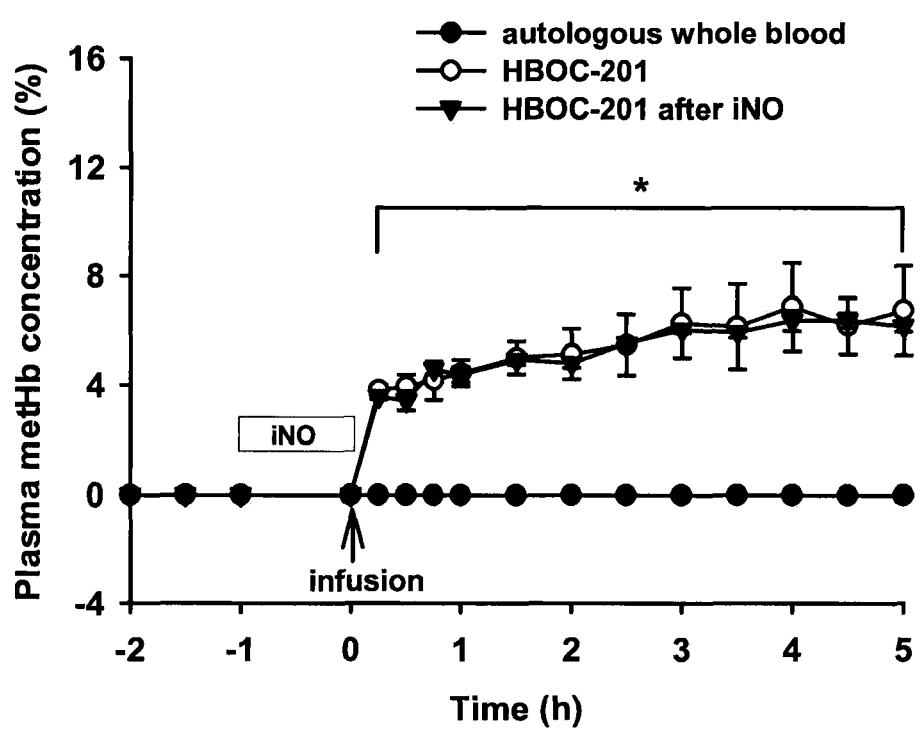
FIG. 15 is a graph depicting plasma methemoglobin concentration in awake lambs breathing air or 80 ppm nitric oxide in air continuously for one hour before infusion of HBOC-201.

Methemoglobin concentration in plasma was measured before and after breathing 80 ppm nitric oxide for one hour (and before and after infusion of autologous whole blood or HBOC-201). Breathing 80 ppm nitric oxide continuously for one hour before infusion of HBOC-201 (and terminating nitric oxide inhalation at the time of infusion) did not result in an increase in plasma methemoglobin as compared to lambs that received HBOC-201 but did not inhale nitric oxide (FIG. 15; *$p<0.05$ autologous whole blood differs from HBOC-201 with or without inhaled nitric oxide pretreatment).

Example 7

Continuous Nitric Oxide Inhalation Before Infusion of HBOC-201 Coupled with Low Dose Nitric Oxide Inhalation Subsequent to HBOC-201 Infusion, Prevents Induction of Pulmonary Vasoconstriction in Lambs Three groups of awake, spontaneously breathing lambs were studied:
(1) "Autologous whole blood" animals received an infusion of 37° C. autologous whole blood (12 ml/kg over 20 minutes) while breathing at $FiO_2$=0.3 (n=3); (2) "HBOC-201" animals received an infusion of 37° C. HBOC-201 (12 ml/kg over 20 minutes) while breathing at $FiO_2$=0.3 (n=3); and (3) "HBOC-201 after high and low dose iNO" animals inhaled 80 ppm nitric oxide at $FiO_2$=0.3 for one hour before receiving an infusion of HBOC-201 (12 ml/kg over 20 minutes), which was followed by breathing 5 ppm nitric oxide at $FiO_2$=0.3 for two hours, which was followed by breathing at $FiO_2$=0.3 (and discontinued inhalation of nitric oxide gas) for another one hour (n=4).

Figure 16:
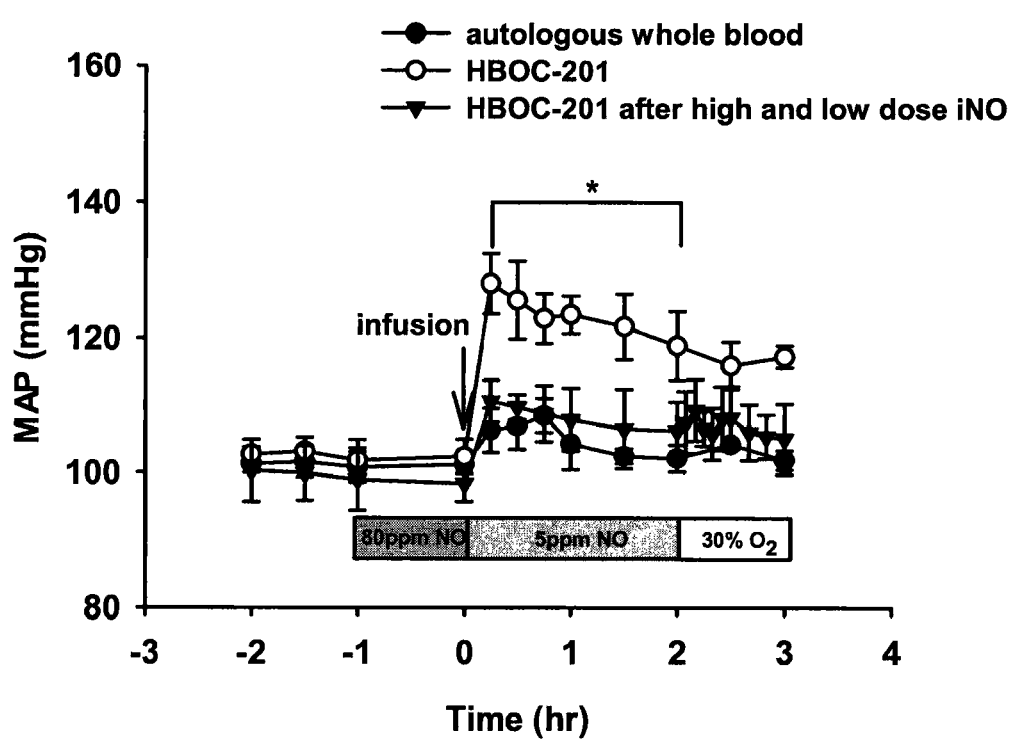
FIG. 16 is a graph depicting mean systemic arterial pressure (MAP) in awake lambs breathing air or 80 ppm nitric oxide in air continuously for one hour before, and 5 ppm nitric oxide in air for two hours subsequent to, infusion of HBOC-201 or given an infusion of 37 degrees C. autologous blood stored in heparin for 2 days.
Figure 17:
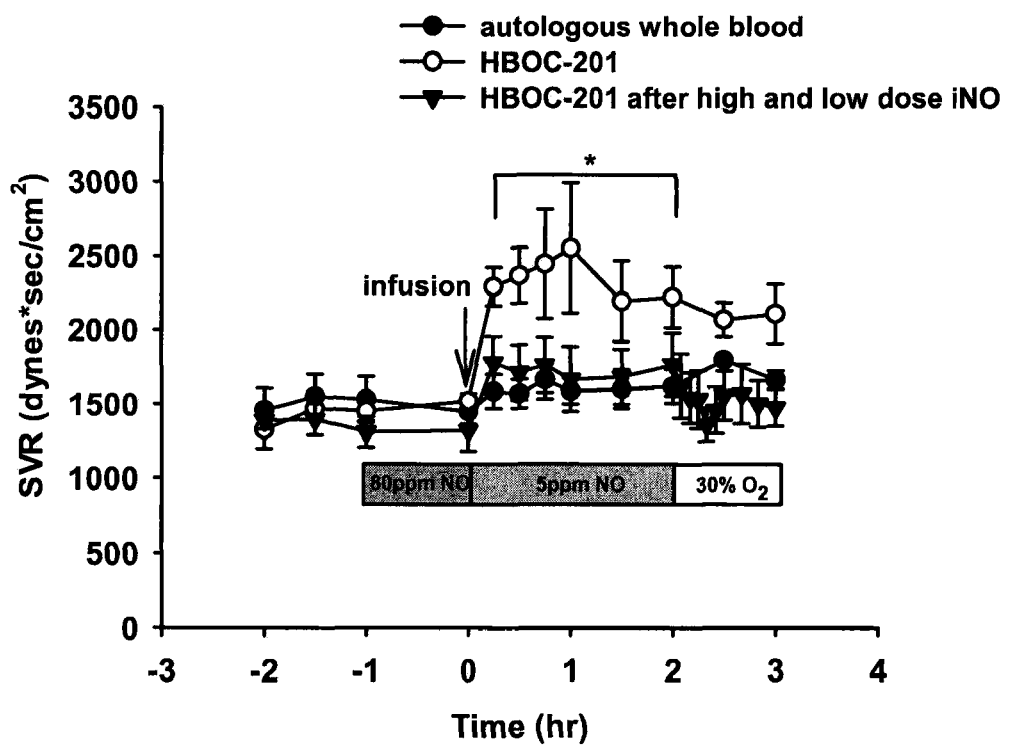
FIG. 17 is a graph depicting systemic vascular resistance (SVR) in awake lambs breathing air or 80 ppm nitric oxide in air continuously for one hour before, and 5 ppm nitric oxide in air for two hours subsequent to, infusion of HBOC-201 or given an infusion of autologous blood.

Mean arterial pressure and systemic vascular resistance were measured before and after infusion of autologous whole blood or HBOC-201. Breathing 80 ppm nitric oxide continuously for one hour before infusion of HBOC-201, followed by breathing 5 ppm nitric oxide after the infusion, blocked the increase in mean arterial pressure (FIG. 16; *$p<0.05$ HBOC-201 differs from autologous blood and from HBOC-201 with inhaled nitric oxide) and systemic vascular resistance (FIG. 17; *$p<0.05$ HBOC-201 differs from autologous blood and from HBOC-201 with inhaled nitric oxide) that otherwise occurred in lambs after HBOC-201 infusion (or HBOC-201 infusion after pretreatment with one hour of inhaled NO at 80 ppm).

Figure 18:
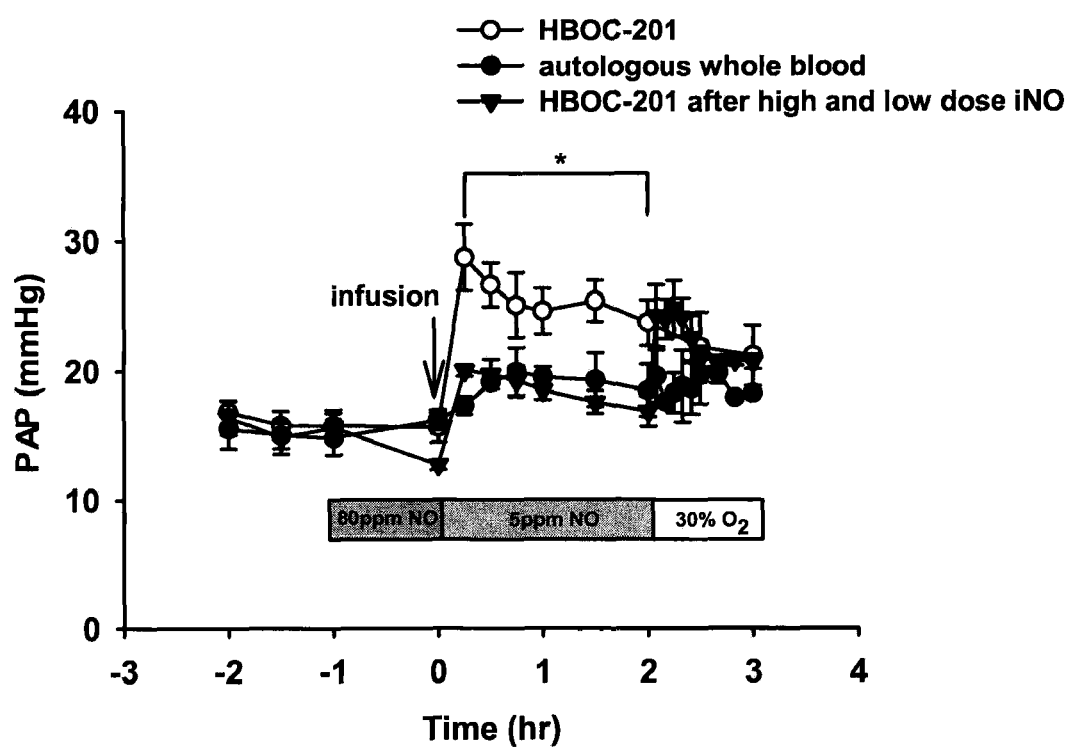
FIG. 18 is a graph depicting mean pulmonary arterial pressure (PAP) in awake lambs breathing air or 80 ppm nitric oxide in air continuously for one hour before, and 5 ppm nitric oxide in air for two hours subsequent to, infusion of HBOC-201 or given an infusion of autologous blood.
Figure 19:
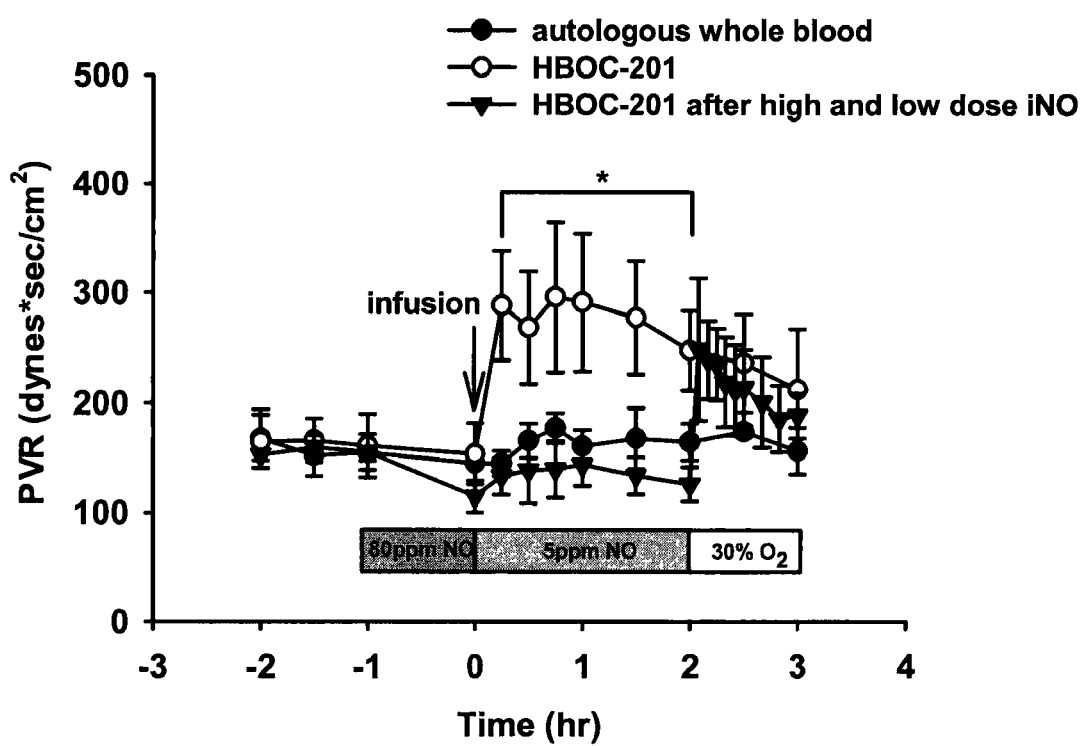
FIG. 19 is a graph depicting pulmonary vascular resistance (PVR) in awake lambs breathing air or 80 ppm nitric oxide in air continuously for one hour before, and 5 ppm nitric oxide in air for two hours subsequent to, infusion of HBOC-201 or given an infusion of autologous blood.

Mean pulmonary arterial pressure and pulmonary vascular resistance were measured before and after infusion of autologous whole blood or HBOC-201. Breathing 80 ppm nitric oxide continuously for one hour before infusion of HBOC-201, followed by breathing 5 ppm nitric oxide after the infusion, blocked the increase in pulmonary arterial pressure (FIG. 18; *$p<0.05$ HBOC-201 differs from autologous blood and from HBOC-201 after inhaled nitric oxide) and pulmonary vascular resistance (FIG. 19; *$p<0.05$ HBOC-201 differs from autologous blood and from HBOC-201 after inhaled nitric oxide) that otherwise occurred after HBOC-201 infusion or after HBOC-201 infusion after pretreatment by breathing 80 ppm NO for one hour. However, pulmonary hypertension rebounded (in animals that were administered HBOC-201) after inhalation of 5 ppm nitric oxide was abruptly discontinued.

Figure 20:
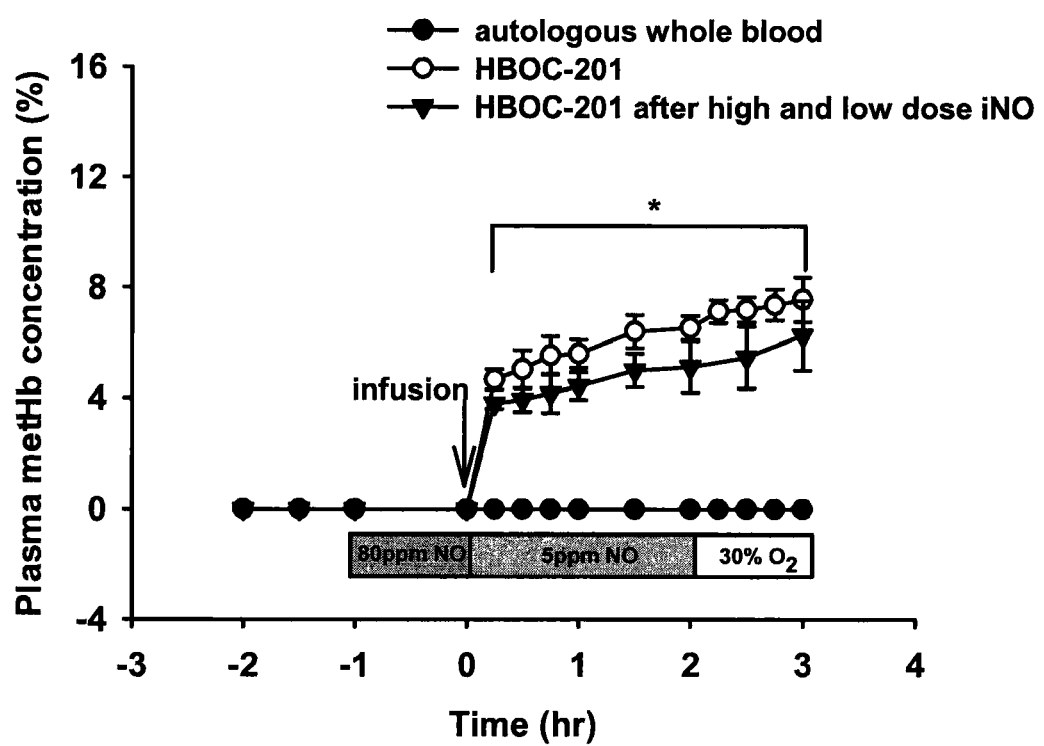
FIG. 20 is a graph depicting plasma methemoglobin concentration in awake lambs breathing air or 80 ppm nitric oxide in air continuously for one hour before, and 5 ppm nitric oxide in air for two hours subsequent to, infusion of HBOC-201.

Plasma methemoglobin concentration was measured before and after breathing nitric oxide at various concentrations (and before and after infusion of autologous whole blood or HBOC-201). Breathing 80 ppm nitric oxide continuously for one hour before infusion of HBOC-201, followed by breathing 5 ppm nitric oxide after the infusion, did not result in an increase in plasma methemoglobin as compared to animals that received HBOC-201 but did not inhale nitric oxide (FIG. 20).

Figure 21:
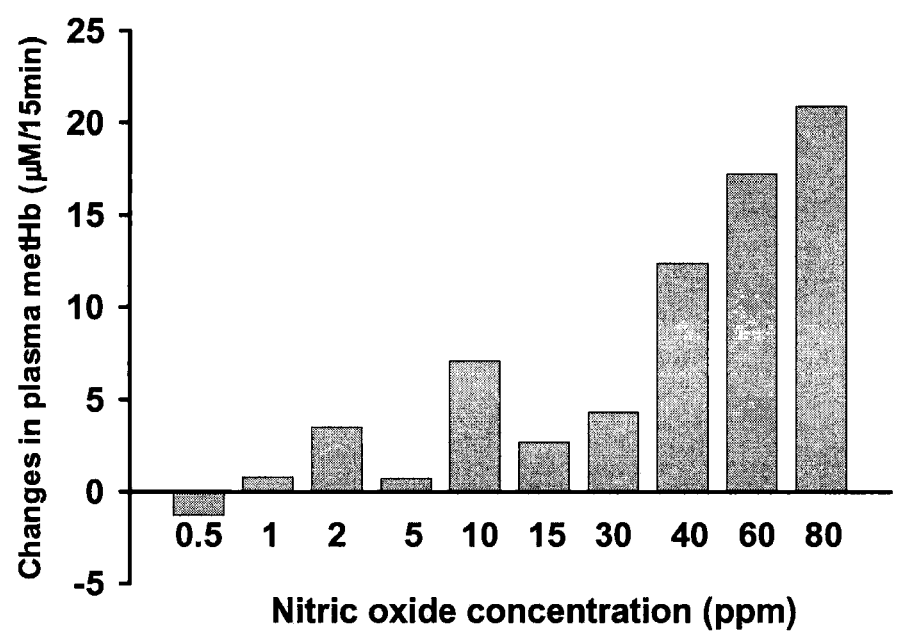
FIG. 21 is a graph depicting changes in plasma methemoglobin levels in an awake lamb breathing various concentrations of nitric oxide in air continuously for 15 minutes after infusion of HBOC-201.

A dose response study was performed to evaluate the oxidation of plasma hemoglobin following inhalation of various concentrations of nitric oxide. Plasma methemoglobin levels (μM) were measured in an awake lamb (n=1) after the infusion of HBOC-201 (1.4 g/kg over 20 minutes) while breathing increasing concentrations of nitric oxide. The inhalation of nitric oxide via a tracheostomy persisted for 15 minutes at each level (500 ppb, 1 ppm, 2 ppm, 5 ppm, 10 ppm, 15 ppm, 30 ppm, 40 ppm, 60 ppm, and 80 ppm). The changes in plasma methemoglobin levels before and after breathing at the various inhaled nitric oxide concentrations are depicted in FIG. 21.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of preventing or reducing vasoconstriction in a mammal following administration of red blood cells or a heme-based oxygen carrier, the method comprising:
   administering to the mammal a therapeutic gas comprising gaseous nitric oxide; and
   administering to the mammal, during or after administration of the therapeutic gas, a composition comprising red blood cells or a heme-based oxygen carrier, wherein the therapeutic gas is administered in an amount that (i) is effective to prevent or reduce the occurrence of vasoconstriction in the mammal following administration of the composition comprising red blood cells or a heme-based oxygen carrier and (ii) converts less than 15% of hemoglobin in the mammal's blood to methemoglobin.

2. The method of claim 1, wherein the therapeutic gas is administered to the mammal by inhalation.

3. The method of claim 2, wherein the concentration of gaseous nitric oxide in the therapeutic gas is at least 20 ppm.

4. The method of claim 2, wherein the concentration of gaseous nitric oxide in the therapeutic gas is at least 40 ppm.

5. The method of claim 2, wherein the concentration of gaseous nitric oxide in the therapeutic gas is at least 80 ppm.

6. The method of claim 2, wherein the concentration of gaseous nitric oxide in the therapeutic gas is in the range of 100 ppm to 500 ppm.

7. The method of claim 2, wherein the therapeutic gas is administered to the mammal continuously for at least three minutes.

8. The method of claim 2, wherein the therapeutic gas is administered to the mammal continuously for at least 15 minutes.

9. The method of claim 2, wherein the therapeutic gas is administered to the mammal continuously for at least one hour.

10. The method of claim 1, wherein administration of the therapeutic gas is terminated before administration of the composition comprising red blood cells or a heme-based oxygen carrier.

11. The method of claim 10, wherein administration of the therapeutic gas is terminated at least three minutes before administration of the composition comprising red blood cells or a heme-based oxygen carrier.

12. The method of claim 10, wherein administration of the therapeutic gas is terminated at least 15 minutes before administration of the composition comprising red blood cells or a heme-based oxygen carrier.

13. The method of claim 1, wherein administration of the therapeutic gas is terminated after administration of the composition comprising red blood cells or a heme-based oxygen carrier.

14. The method of claim 1, wherein the concentration of gaseous nitric oxide in the therapeutic gas is reduced during the course of the administration.

15. The method of claim 14, wherein the concentration of gaseous nitric oxide in the therapeutic gas is reduced at a constant rate during all or part of the administration.

16. The method of claim 14, wherein the concentration of gaseous nitric oxide in the therapeutic gas is reduced by one or more step-wise reductions during the course of the administration.

17. The method of claim 1, wherein the method further comprises administering to the mammal a phosphodiesterase inhibitor, a soluble guanylate cyclase sensitizer, or a phosphodiesterase inhibitor and a soluble guanylate cyclase sensitizer.

18. The method of claim 17, wherein the phosphodiesterase inhibitor, the soluble guanylate cyclase sensitizer, or the phosphodiesterase inhibitor and the soluble guanylate cyclase sensitizer are administered to the mammal after administration of the composition comprising red blood cells or a heme-based oxygen carrier.

19. The method of claim 17, wherein the phosphodiesterase inhibitor is sildenafil, tadalafil, or vardenafil.

20. The method of claim 1, wherein the composition comprises red blood cells.

21. The method of claim 20, wherein the red blood cells are autologous red blood cells.

22. The method of claim 20, wherein the red blood cells are allogeneic red blood cells.

23. The method of claim 20, wherein the red blood cells have been stored for at least three hours after removal from a donor and prior to administration to the mammal.

24. The method of claim 20, wherein the red blood cells have been stored for at least 24 hours after removal from a donor and prior to administration to the mammal.

25. The method of claim 20, wherein the red blood cells have been stored for at least 14 days after removal from a donor and prior to administration to the mammal.

26. The method of claim 20, wherein the red blood cells have been stored for at least 21 days after removal from a donor and prior to administration to the mammal.

27. The method of claim 20, wherein the red blood cells have been stored for at least 28 days after removal from a donor and prior to administration to the mammal.

28. The method of claim 1, wherein the composition comprises a heme-based oxygen carrier.

29. The method of claim 28, wherein the heme-based oxygen carrier is a heme-albumin-based oxygen carrier or a heme-dextran-based oxygen carrier.

30. The method of claim 28, wherein the heme-based oxygen carrier is a hemoglobin-based oxygen carrier.

31. The method of claim 30, wherein the hemoglobin-based oxygen carrier comprises a modified hemoglobin.

32. The method of claim 30, wherein the hemoglobin-based oxygen carrier comprises cross-linked hemoglobin.

33. The method of claim 30, wherein the hemoglobin-based oxygen carrier comprises cross-linked polyhemoglobin, cross-linked tetrameric hemoglobin, conjugated hemoglobin, recombinant hemoglobin, or encapsulated hemoglobin.

34. The method of claim 30, wherein the hemoglobin-based oxygen carrier comprises human hemoglobin.

35. The method of claim 30, wherein the hemoglobin-based oxygen carrier comprises bovine or porcine hemoglobin.

36. The method of claim 30, wherein the composition comprising the hemoglobin-based oxygen carrier is administered to the mammal by intravenous, intraarterial, or intraosseous infusion.

37. The method of claim 1, wherein the mammal has an anemia.

38. The method of claim 37, wherein the anemia is severe acute anemia.

39. The method of claim 1, wherein the mammal has suffered blood loss as a result of surgery.

40. The method of claim 39, wherein the surgery is cardiac or orthopedic surgery.

41. The method of claim 1, wherein the mammal has suffered blood loss as a result of trauma.

42. The method of claim 1, wherein the mammal has ischemic heart disease or has suffered an acute ischemic event.

43. The method of claim 42, wherein the mammal has suffered a myocardial infarction or a stroke.

44. The method of claim 42, wherein the acute ischemic event is caused by surgical revascularization, transplantation, or angioplasty.

45. The method of claim 1, wherein the mammal exhibits vasospasm of an organ prior to treatment.

46. The method of claim 45, wherein the organ is the brain, heart, kidney, liver, or an organ of the gastrointestinal tract.

47. The method of claim 1, wherein the mammal is a human.

48. The method of claim 1, wherein the therapeutic gas is inhaled in the absence of tobacco smoke.

49. A method of preventing or reducing systemic and pulmonary vasoconstriction in a mammal following administration of red blood cells or a heme-based oxygen carrier, the method comprising:

administering to the mammal a first therapeutic gas comprising gaseous nitric oxide;

administering to the mammal, during or after administration of the first therapeutic gas, a composition comprising red blood cells or a heme-based oxygen carrier; and administering to the mammal, after administration of the first therapeutic gas, a second therapeutic gas comprising gaseous nitric oxide, wherein the concentration of gaseous nitric oxide in the second therapeutic gas is less than the concentration of gaseous nitric oxide in the first therapeutic gas, and wherein administration of the second therapeutic gas begins (i) after administration of the composition comprising red blood cells or a heme-based oxygen carrier, or (ii) before or during administration of the composition comprising red blood cells or a heme-based oxygen carrier and continues after administration of the composition comprising red blood cells or a heme-based oxygen carrier, wherein the first and second therapeutic gases are administered in amounts that (i) are effective to prevent or reduce the occurrence of systemic and pulmonary vasoconstriction in the mammal following administration of the composition comprising red blood cells or a heme-based oxygen carrier and (ii) convert less than 15% of hemoglobin in the mammal's blood to methemoglobin.

50. The method of claim 49, wherein the first and second therapeutic gases are administered to the mammal by inhalation.

51. The method of claim 50, wherein the concentration of gaseous nitric oxide in the first therapeutic gas is at least 20 ppm.

52. The method of claim 50, wherein the concentration of gaseous nitric oxide in the first therapeutic gas is at least 40 ppm.

53. The method of claim 50, wherein the concentration of gaseous nitric oxide in the first therapeutic gas is at least 80 ppm.

54. The method of claim 50, wherein the concentration of gaseous nitric oxide in the first therapeutic gas is in the range of 80 ppm to 500 ppm.

55. The method of claim 50, wherein the first therapeutic gas is administered to the mammal continuously for at least three minutes.

56. The method of claim 50, wherein the first therapeutic gas is administered to the mammal continuously for at least 15 minutes.

57. The method of claim 50, wherein the first therapeutic gas is administered to the mammal continuously for at least one hour.

58. The method of claim 50, wherein the concentration of gaseous nitric oxide in the second therapeutic gas is least 5 ppm.

59. The method of claim 50, wherein the concentration of gaseous nitric oxide in the second therapeutic gas is less than 40 ppm.

60. The method of claim 50, wherein the concentration of gaseous nitric oxide in the second therapeutic gas is less than 20 ppm.

61. The method of claim 50, wherein the concentration of gaseous nitric oxide in the second therapeutic gas is in the range of 5 ppm to 40 ppm.

62. The method of claim 50, wherein the second therapeutic gas is administered to the mammal continuously for at least three minutes.

63. The method of claim 50, wherein the second therapeutic gas is administered to the mammal continuously for at least 15 minutes.

64. The method of claim 50, wherein the second therapeutic gas is administered to the mammal continuously for at least one hour.

65. The method of claim 50, wherein the second therapeutic gas is administered to the mammal continuously for at least two hours.

66. The method of claim 50, wherein the second therapeutic gas is administered to the mammal continuously for at least 24 hours.

67. The method of claim 50, wherein administration of the first therapeutic gas is terminated before administration of the composition comprising red blood cells or a heme-based oxygen carrier.

68. The method of claim 67, wherein administration of the first therapeutic gas is terminated at least three minutes before administration of the composition comprising red blood cells or a heme-based oxygen carrier.

69. The method of claim 67, wherein administration of the first therapeutic gas is terminated at least 15 minutes before administration of the composition comprising red blood cells or a heme-based oxygen carrier.

70. The method of claim 50, wherein administration of the first therapeutic gas is terminated after administration of the composition comprising red blood cells or a heme-based oxygen carrier.

71. The method of claim 50, wherein administration of the second therapeutic gas begins before or during administration of the composition comprising red blood cells or a heme-based oxygen carrier and continues after administration of the composition comprising red blood cells or a heme-based oxygen carrier.

72. The method of claim 50, wherein administration of the second therapeutic gas begins after administration of the composition comprising red blood cells or a heme-based oxygen carrier.

73. The method of claim 50, wherein a single gas delivery device is used to deliver both the first therapeutic gas and the second therapeutic gas to the mammal, and wherein the concentration of administered gaseous nitric oxide is reduced during administration of the first therapeutic gas, thereby resulting in the second therapeutic gas having a concentration of gaseous nitric oxide that is less than the concentration of gaseous nitric oxide in the first therapeutic gas.

74. The method of claim 73, wherein the concentration of administered gaseous nitric oxide is reduced at a constant rate subsequent to the initiation of the administration of the first therapeutic gas, thereby resulting in the second therapeutic gas.

75. The method of claim 73, wherein the concentration of administered gaseous nitric oxide is reduced by a step-wise reduction subsequent to the initiation of the administration of the first therapeutic gas, thereby resulting in the second therapeutic gas.

76. The method of claim 50, wherein the concentration of gaseous nitric oxide in the first therapeutic gas is in the range of 20 ppm to 500 ppm and the concentration of gaseous nitric oxide in the second therapeutic gas is in the range of 500 ppb to 40 ppm.

77. A method of preventing or reducing vasoconstriction in a mammal following administration of red blood cells or a heme-based oxygen carrier, the method comprising:

administering to the mammal a nitric oxide-releasing compound; and administering to the mammal, during or after administration of the nitric-oxide releasing compound, a composition comprising red blood cells or a heme-based oxygen carrier, wherein the nitric oxide-releasing compound is administered in an amount that (i) is effective to prevent or reduce the occurrence of vasoconstriction in the mammal following administration of the composition comprising red blood cells or a heme-based oxygen carrier and (ii) converts less than 15% of hemoglobin in the mammal's blood to methemoglobin.

78. The method of claim 77, wherein the nitric oxide-releasing compound comprises nitrite.

79. A gas delivery device comprising:
a lumen configured to route a gas into the respiratory system of a mammal;
a first meter configured to measure the concentration of nitric oxide gas present in the lumen;
a second meter configured to measure the rate of gas flow in the lumen; and
a dosimeter that integrates the concentration of nitric oxide measured in the lumen with the rate of gas flow measured in the lumen to determine the amount of nitric oxide delivered by the device to the respiratory system of the mammal.

80. The device of claim 79, further comprising a vessel comprising pressurized gas comprising at least 1 ppm nitric oxide, wherein the vessel has a mechanism for controllably releasing the pressurized gas into the lumen or into a chamber in communication with the lumen.

81. The device of claim 80, wherein the release of the pressurized gas is triggered by negative inspiratory pressure of the mammal, and the pressurized gas release is limited to the inspiratory cycle of respiration, thereby reducing the delivery of inspired gas to the respiratory dead space and reducing the requirement for inspired gas.

* * * * *